US007603282B2

(12) United States Patent
Imai et al.

(10) Patent No.: US 7,603,282 B2
(45) Date of Patent: Oct. 13, 2009

(54) COMMUNICATION SYSTEM FOR INFORMATION OF MEDICAL DOCTOR'S QUESTIONS TO PATIENTS, TERMINAL APPARATUS FOR MEDICAL DOCTOR AND TERMINAL APPARATUS FOR PATIENT

(75) Inventors: Hirohisa Imai, Nara (JP); Hiroyoshi Nomura, Soraku-gun (JP); Kiyoshi Kanazawa, Katano (JP); Jinsei Miyazaki, Higashiosaka (JP); Shunichi Nagamoto, Nara (JP)

(73) Assignee: Panasonic Corporation, Osaka (JP)

( * ) Notice: Subject to any disclaimer, the term of this patent is extended or adjusted under 35 U.S.C. 154(b) by 966 days.

(21) Appl. No.: 10/058,732

(22) Filed: Jan. 30, 2002

(65) Prior Publication Data

US 2008/0172245 A1 Jul. 17, 2008

(51) Int. Cl.
*G06Q 10/00* (2006.01)
(52) U.S. Cl. .............................. 705/2; 705/3; 707/104.1
(58) Field of Classification Search ................. 705/2–3; 707/104.1
See application file for complete search history.

(56) References Cited

U.S. PATENT DOCUMENTS

| | | | | |
|---|---|---|---|---|
| 4,428,733 A | * | 1/1984 | Kumar-Misir | 434/363 |
| 5,517,405 A | * | 5/1996 | McAndrew et al. | 706/45 |
| 5,572,421 A | * | 11/1996 | Altman et al. | 705/3 |
| 5,596,994 A | * | 1/1997 | Bro | 600/545 |
| 5,845,255 A | | 12/1998 | Mayaud | |
| 6,014,630 A | * | 1/2000 | Jeacock et al. | 705/3 |
| 6,022,315 A | * | 2/2000 | Iliff | 600/300 |
| 6,047,259 A | * | 4/2000 | Campbell et al. | 705/3 |
| 6,101,478 A | * | 8/2000 | Brown | 705/2 |

(Continued)

FOREIGN PATENT DOCUMENTS

JP 61-286974 12/1986

(Continued)

OTHER PUBLICATIONS

Gordon, Thomas. "Making Your Patient Your Partner: Communications Skills for Doctors and Other Caregivers" Copyright 1995. Auburn House. p. 85-86.*

(Continued)

*Primary Examiner*—Gerald J. O'Connor
*Assistant Examiner*—Lena Najarian
(74) *Attorney, Agent, or Firm*—Wenderoth, Lind & Ponack, L.L.P.

(57) ABSTRACT

A communication system for providing information of a medical doctor's questions to patients includes a medical doctor terminal apparatus, a patient terminal apparatus, and a database server apparatus for storing question sets for the medical doctor's questions to patients, where the medical doctor terminal apparatus, patient terminal apparatus and database server apparatus are connected through a communication network. The patient terminal apparatus generates question programs for making inquiries about the medical doctor's questions to patients in accordance with the question sets received from the database server apparatus, displays the questions for the medical doctor's questions to patients by execution of the generated question programs, enters answer data to the displayed questions, transmits the entered answer data to the database server apparatus, and stores the transmitted answer data in the database server apparatus. The medical doctor terminal apparatus receives the stored answer data by accessing the database server apparatus, and displays the received answer data thereon.

24 Claims, 36 Drawing Sheets

U.S. PATENT DOCUMENTS

| | | | |
|---|---|---|---|
| 6,108,665 A * | 8/2000 | Bair et al. | 707/104.1 |
| 6,151,581 A * | 11/2000 | Kraftson et al. | 705/3 |
| 6,196,970 B1 * | 3/2001 | Brown | 600/300 |
| 6,249,809 B1 * | 6/2001 | Bro | 709/217 |
| 6,270,456 B1 * | 8/2001 | Iliff | 600/300 |
| 6,283,761 B1 * | 9/2001 | Joao | 434/236 |
| 6,381,029 B1 * | 4/2002 | Tipirneni | 358/1.14 |
| 6,757,898 B1 | 6/2004 | Ilsen et al. | |
| 6,820,235 B1 | 11/2004 | Bleicher et al. | |
| 6,850,889 B1 * | 2/2005 | Zayas, Jr. | 705/3 |
| 2001/0034615 A1 * | 10/2001 | Wilkinson et al. | 705/2 |
| 2002/0019747 A1 * | 2/2002 | Ware et al. | 705/2 |
| 2002/0022975 A1 * | 2/2002 | Blasingame et al. | 705/3 |
| 2002/0035486 A1 * | 3/2002 | Huyn et al. | 705/3 |
| 2002/0035487 A1 * | 3/2002 | Brummel et al. | 705/3 |
| 2002/0049684 A1 | 4/2002 | Nagamoto et al. | |
| 2002/0128870 A1 * | 9/2002 | Whitson | 705/3 |
| 2002/0133377 A1 * | 9/2002 | Brown | 705/3 |
| 2002/0133502 A1 * | 9/2002 | Rosenthal et al. | 707/104.1 |
| 2003/0017440 A1 * | 1/2003 | Bergey et al. | 434/262 |
| 2003/0046305 A1 * | 3/2003 | Clarkson | 707/104.1 |
| 2003/0130873 A1 * | 7/2003 | Nevin et al. | 705/3 |
| 2005/0149852 A1 | 7/2005 | Bleicher et al. | |

FOREIGN PATENT DOCUMENTS

| | | |
|---|---|---|
| JP | 9-84771 | 3/1997 |
| JP | 10-143578 | 5/1998 |
| JP | 2000-276537 | 10/2000 |
| JP | 2001-273365 | 10/2001 |
| JP | 2002-15071 | 1/2002 |
| WO | 99/63473 | 12/1999 |
| WO | 01/53959 | 7/2001 |
| WO | 01/93140 | 12/2001 |

OTHER PUBLICATIONS

Supplementary European Search Report issued Nov. 6, 2008 in European Application No. 02711255.6.

* cited by examiner

TERMINAL APPARATUS 10 FOR MEDICAL DOCTOR

TERMINAL APPARATUS 20 FOR PATIENT

DATABASE SERVER APPARATUS 30

PATIENT INFORMATION MEMORY 304a

QUESTION SET MEMORY 304b

Fig.7

| QUESTIONS | PATIENTS | | | |
|---|---|---|---|---|
| | No.1 | No.2 | No.3 | ------ |
| No.1 | ○ | ○ | | |
| GOAL | | | | |
| No.2 | ○ | | | ------ |
| GOAL | YES | | | |
| No.3 | | | ○ | |
| GOAL | | | | |
| ⋮ | ⋮ | ⋮ | | |

↑ LINKING DATA MEMORY 304c

Fig.8

| DATE AND TIME OF ANSWER | PATIENT No. | ANSWER No. | GOAL | ANSWER |
|---|---|---|---|---|
| 2001/12/03,12:00 | 1 | 1 | | 2 : NO |
| 2001/12/03,12:00 | 1 | 2 | YES | 1 : YES |
| 2001/12/03,13:00 | 2 | 1 | | 1 : YES |
| 2001/12/03,14:00 | 3 | 3 | | 2 : SLEPT |

↑ ANSWER DATA MEMORY 304d

Fig.9 DATA FORMAT OF QUESTION SET

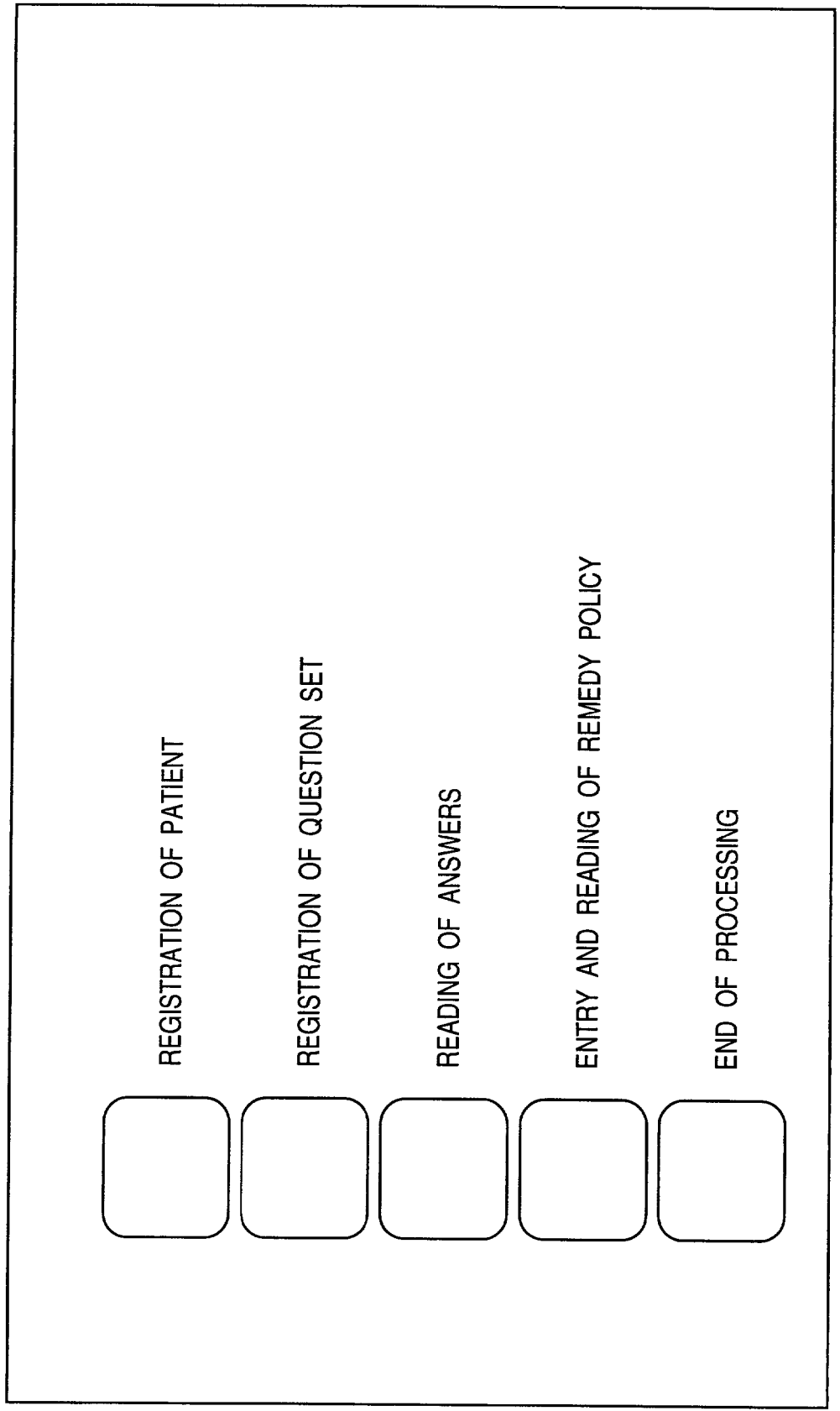
Fig.24 EXAMPLE OF SCREEN OF TERMINAL APPARATUS 10 FOR MEDICAL DOCTOR : MENU SCREEN

Fig.25

EXAMPLE OF SCREEN OF TERMINAL APPARATUS 10 FOR MEDICAL DOCTOR : SCREEN OF PATIENT REGISTRATION

PATIENT No.  XXXXX      NAME

DATE OF BIRTH                   SEX

| | REQUIRED | GOAL | QUESTION |
|---|---|---|---|
| No.1 | ○ | | DO YOU HAVE HEADACHE ? |
| No.2 | ○ | YES | DID YOU DO EXERCISE FOR 30 MINUTES OR MORE ? |
| No.3 | ○ | | DID YOU SLEEP WELL LAST NIGHT ? |
| No.4 | ○ | LESS THAN 1 | DID YOU DRINK BEER ? |
| No.5 | ○ | | WHICH TIME PERIOD DID YOU EAT TODAY ? |
| No.6 | ○ | ALL | WHICH FOOD DID YOU EAT TODAY ? |
| No.7 | | | PLEASE ENTER PEAK FLOW VALUE |
| No.8 | ○ | 10000 OR MORE | PLEASE ENTER NUMBER OF STEPS |
| No.9 | | | HOW MANY TIMES DID YOU URINATE TODAY ? |
| No.10 | | | HOW MANY CIGARETTES DID YOU SMOKE ? |

REGISTRATION

Fig.26

EXAMPLE OF SCREEN OF TERMINAL APPARATUS 10 FOR MEDICAL DOCTOR : SCREEN OF QUESTION SET REGISTRATION

QUESTION No.    YY
ANSWER FORM    ⊘ SINGLE SELECTION TYPE   ○ PLURAL SELECTION TYPE   ○ NUMERICAL ENTRY VALUE   ○ INCREMENT OR DECREMENT VALUE ENTRY TYPE

QUESTION SENTENCE

SELECTION SENTENCE
| 1 |
| 2 |
| 3 |
| 4 |

PATIENT SELECTION

○ xxx   ○ xxx   ○ xxx   ○ xxx
○ xxx   ○ xxx   ⊘ xxx   ○ xxx
○ xxx   ○ xxx   ○ xxx   ○ xxx (REGISTRATION)

Fig.27 EXAMPLE OF SCREEN OF TERMINAL APPARATUS 10 FOR MEDICAL DOCTOR : SCREEN OF ANSWER READING

PATIENT SELECTION

| | | | |
|---|---|---|---|
| ○xxx | ○xxx | ○xxx | ○xxx |
| ○xxx | ○xxx | ⊘xxx | ○xxx |
| ○xxx | ○xxx | ○xxx | ○xxx |

251

| DATE AND TIME | LINKING | GOAL | QUESTION | ANSWER |
|---|---|---|---|---|
| 2001/12/03, 12:00 | REMEDY | | DO YOU HAVE HEADACHE ? | 2:NO |
| 2001/12/03, 12:00 | REMEDY | YES | DID YOU DO EXERCISE FOR 30 MINUTES OR MORE ? | 2:NO |
| 2001/12/03, 12:00 | REMEDY | | DID YOU SLEEP WELL LAST NIGHT ? | 2:SLEPT |
| 2001/12/03, 12:00 | REMEDY | LESS THAN 1 | DID YOU DRINK BEER ? | 2:LESS THAN 2 |
| 2001/12/03, 12:00 | REMEDY | ALL | WHICH TIME PERIOD DID YOU FEEL BADLY ? | 2:6:00~12:00, 2:18:00~24:00 |
| 2001/12/03, 12:00 | REMEDY | | WHICH FOOD DID YOU EAT TODAY ? | 1:GRAIN, 2:MEAT, 5:VEGETABLES |
| 2001/12/03, 12:00 | REMEDY | 10000 OR MORE | PLEASE ENTER NUMBER OF STEPS | 7630 |
| 2001/12/03, 12:00 | REMEDY | YES | DO YOU HAVE HEADACHE ? | 2:NO |
| 2001/12/03, 12:00 | REMEDY | | DID YOU DO EXERCISE FOR 30 MINUTES OR MORE ? | 2:NO |
| 2001/12/03, 12:00 | REMEDY | | DID YOU SLEEP WELL LAST NIGHT ? | 2:SLEPT |

251

( RETRIEVE BY DATE )  ( RETRIEVE BY QUESTION )  ( END OF PROCESSING )

254

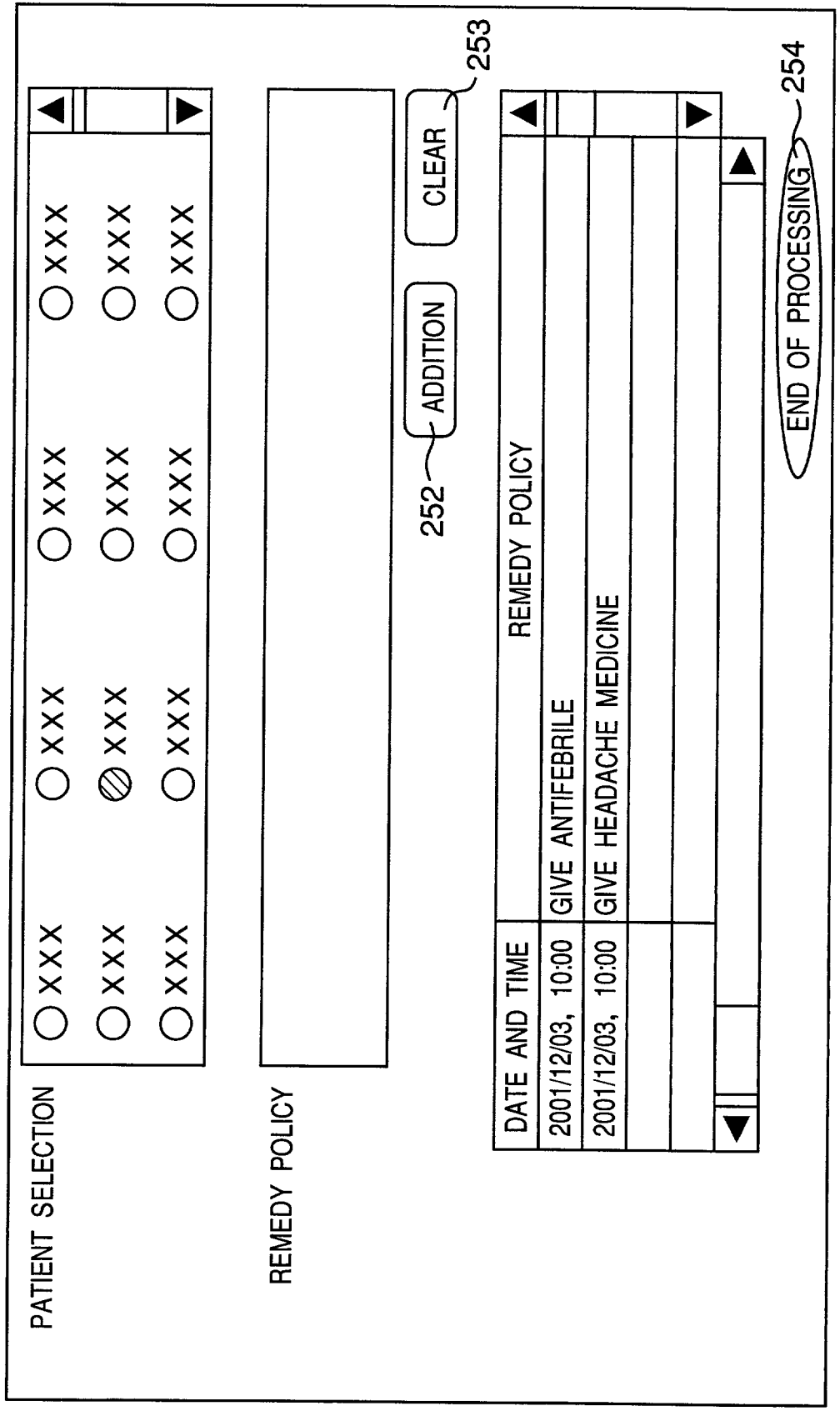
Fig.28 EXAMPLE OF SCREEN OF TERMINAL APPARATUS 10 FOR MEDICAL DOCTOR:
SCREEN OF REMEDY POLICY ENTRY AND READING EXAMPLE OF SCREEN OF TERMINAL APPARATUS 20 FOR PATIENT:
ANSWER FORM SS1 OF SINGLE SELECTION TYPE (SINGLE SELECTION FROM TWO ANSWERS, WITH NO GOAL)

EXAMPLE OF SCREEN OF TERMINAL APPARATUS 20 FOR PATIENT :
ANSWER FORM SS2 OF SINGLE SELECTION TYPE (SINGLE SELECTION FROM TWO ANSWERS, WITH GOAL)

Fig. 31

EXAMPLE OF SCREEN OF TERMINAL APPARATUS 20 FOR PATIENT:
ANSWER FORM SS3 OF SINGLE SELECTION TYPE (SINGLE SELECTION FROM FOUR ANSWERS, WITH NO GOAL)

DID YOU SLEEP WELL LAST NIGHT ?

224 — SLEPT WELL
224 — SLEPT
224 — SLEPT LITTLE
224 — NOT SLEPT

225 — OK

PREVIOUS ANSWER : SLEPT

Fig.32

EXAMPLE OF SCREEN OF TERMINAL APPARATUS 20 FOR PATIENT:
ANSWER FORM SS4 OF SINGLE SELECTION TYPE (SINGLE SELECTION FROM FOUR ANSWERS, WITH GOAL)

DID YOU DRINK BEER ?

224 — LESS THAN 1
224 — LESS THAN 2
224 — LESS THAN 3
224 — 3 OR MORE

225 — OK

PREVIOUS ANSWER : LESS THAN 1
GOAL : LESS THAN 1

Fig.33

EXAMPLE OF SCREEN OF TERMINAL APPARATUS 20 FOR PATIENT:
ANSWER FORM PS1 OF PLURAL SELECTION TYPE (WITH NO GOAL)

WHICH TIME PERIOD DID YOU FEEL BADLY?

0:00~6:00

6:00~12:00

12:00~18:00

18:00~24:00

224

OK — 225

PREVIOUS ANSWER : 6:00~12:00, 18:00~24:00

Fig.34

EXAMPLE OF SCREEN OF TERMINAL APPARATUS 20 FOR PATIENT:
ANSWER FORM PS2 OF PLURAL SELECTION TYPE (WITH GOAL)

WHICH FOOD DID YOU EAT TODAY?

| | | |
|---|---|---|
| 224 GRAIN | 224 MEAT | |
| 224 FISH | 224 DAIRY PRODUCTS | |
| 224 VEGETABLES | 224 FRUITS | |

225 OK

PREVIOUS ANSWER : GRAIN, MEAT, VEGETABLES, FRUITS    GOAL : ALL

Fig.35 EXAMPLE OF SCREEN OF TERMINAL APPARATUS 20 FOR PATIENT:
ANSWER FORM NI1 OF NUMERICAL VALUE ENTRY TYPE (WITH NO GOAL)

PLEASE ENTER PEAK FLOW VALUE

221

222
7 8 9
6 5 4
3 2 1
0 Clear

OK
223

PREVIOUS ANSWER : 650

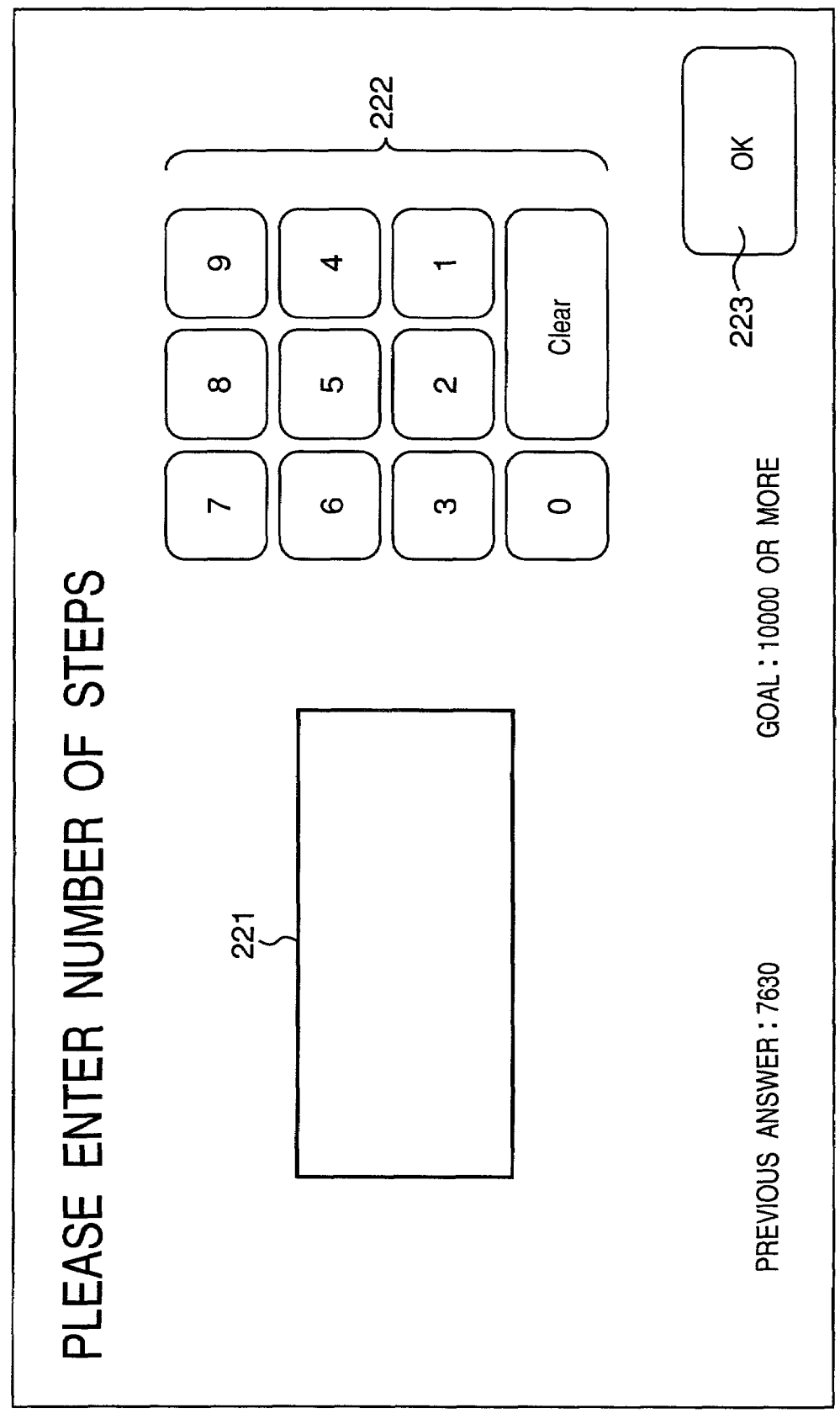
Fig.36 EXAMPLE OF SCREEN OF TERMINAL APPARATUS 20 FOR PATIENT: ANSWER FORM Ni2 OF NUMERICAL VALUE ENTRY TYPE (WITH GOAL)

Fig.37 EXAMPLE OF SCREEN OF TERMINAL APPARATUS 20 FOR PATIENT:
ANSWER FORM II1 OF INCREMENT OR DECREMENT ENTRY TYPE (WITH NO GOAL)
HOW MANY TIMES DID YOU URINATE TODAY?
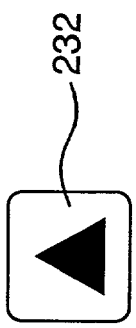—232
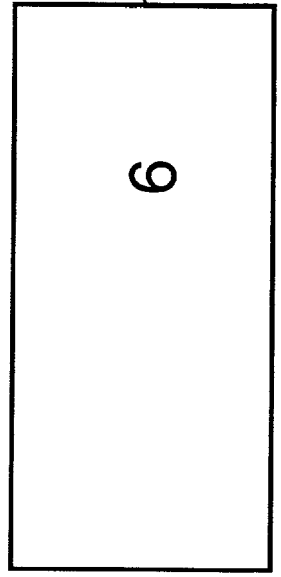—231
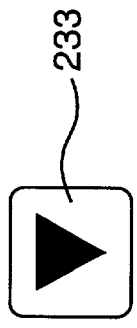—233
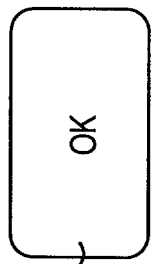—234
PREVIOUS ANSWER : 6

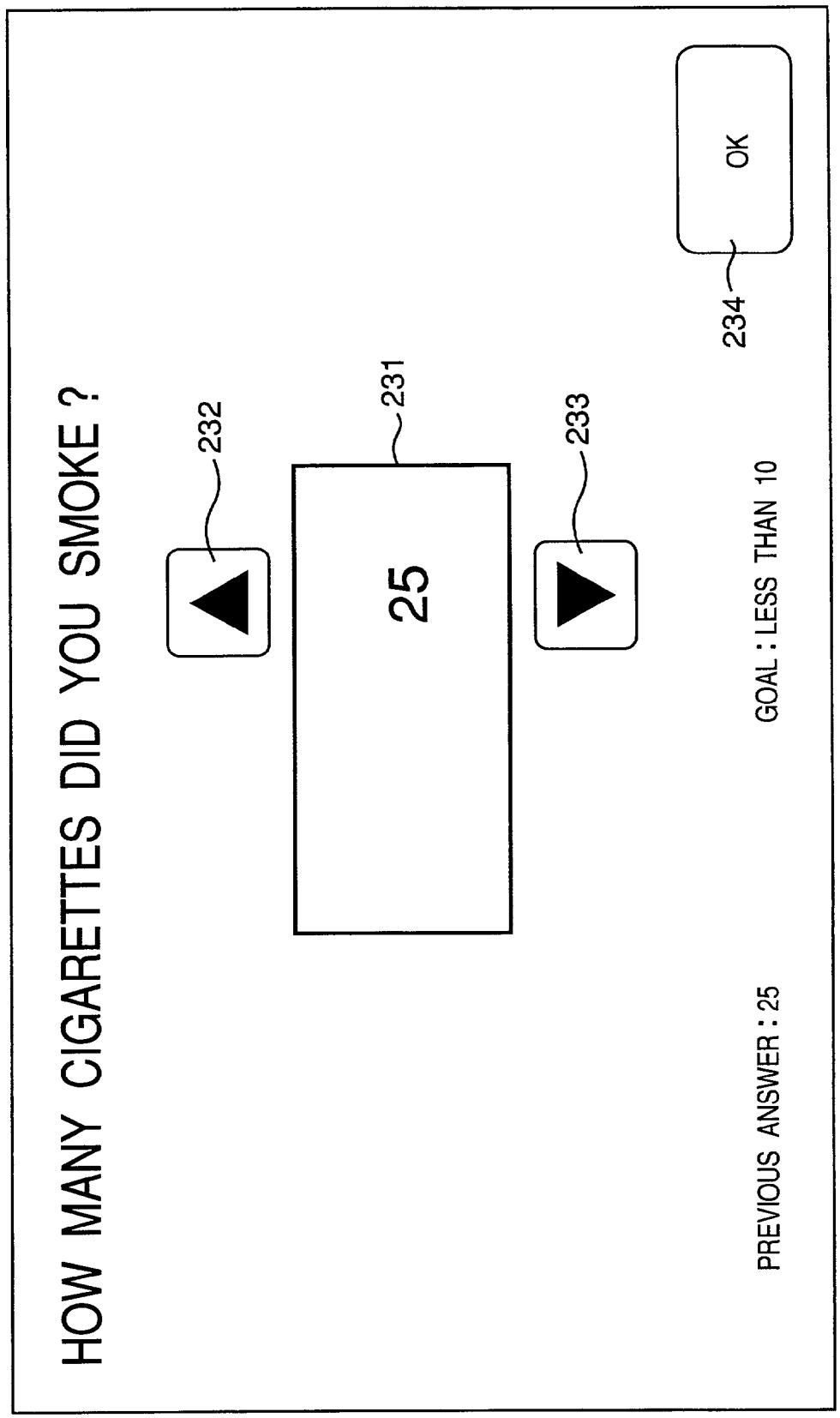

COMMUNICATION SYSTEM FOR INFORMATION OF MEDICAL DOCTOR'S QUESTIONS TO PATIENTS, TERMINAL APPARATUS FOR MEDICAL DOCTOR AND TERMINAL APPARATUS FOR PATIENT

BACKGROUND OF THE INVENTION

1. Field of the Invention

The present invention relates to a communication system for providing information a of medical doctor's questions to patients, in which the communication system includes a terminal apparatus for a medical doctor, a terminal apparatus for a patient and a database server apparatus which are connected to each other through a communication network. More particularly, the present invention relates to a communication system for providing information of a medical doctor's questions to patients for the purpose of remote medical doctor's questions, in which a terminal apparatus for a medical doctor remotely transmits queries to a terminal apparatus for a patient and remotely receives and outputs patient's responses to the queries from the patient terminal apparatus.

2. Description of the Related Art

Conventionally, medical doctor's questions to a patient have required the patient to go to the hospital or clinic or have required the medical doctor to visit the patient's home, so that the medical doctor and the patient have to meet each other face to face, which therefore leads to a considerable loss of time, such as traveling time and waiting time.

In order to solve this problem, a multi-user remote health monitoring system is disclosed in U.S. Pat. No. 6,101,478. In this system, a server apparatus generates and stores script programs containing queries to patients, such as HTML that can be read on the Web. A terminal apparatus for a patient downloads the script program stored in the server apparatus and thereafter executes the script program. Then, the patient answers the queries displayed on a display of the patient terminal apparatus, and thereafter, answer data is transmitted from the patient terminal apparatus to the server apparatus.

Moreover, a remote diagnostic system is disclosed in Japanese Patent Laid-open Publication No. 9-84771. In this system, a center apparatus comprising a computer transmits a checklist containing medical doctor's questions for a patient to a remote terminal apparatus. The remote terminal apparatus performs a measurement on the patient and informs the patient of the medical doctor's questions in accordance with the received checklist according to patient and thereafter transmits the patient's measurements and answers to the center apparatus, which then stores the measurements and answers to permit a medical doctor to carry out a diagnosis based on the measurements and answers.

However, these systems of the prior arts have a problem in that the systems cannot retain security since the systems are configured to transmit the script program containing queries or the checklist containing medical doctor's questions for the patient to the patient remote terminal apparatus.

SUMMARY OF THE INVENTION

It is an essential object of the present invention to solve the above-mentioned problems, and provide a communication system for providing information of a medical doctor's questions to patients, a terminal apparatus for a medical doctor and a terminal apparatus for a patient, which are capable of retaining security, as compared to the systems of the prior art.

According to the present invention, a communication system for providing information of a medical doctor's questions to patients includes a medical doctor terminal apparatus, a patient terminal apparatus, and a database server apparatus for storing question sets for the medical doctor's questions to patients. The medical terminal apparatus, the patient terminal apparatus and the database server apparatus are connected to each other through a communication network. In this case, the terminal apparatus for patient includes: generating means for generating question programs for making inquiries about medical doctor's questions to patients in accordance with the question sets received from the database server apparatus; displaying means for displaying questions for medical doctor's questions to patients by execution of the generated question programs; entering means for entering answer data to the displayed questions; and transmitting means for transmitting the entered answer data to the database server apparatus, and storing the transmitted answer data in the database server apparatus. The terminal apparatus for medical doctor includes receiving means for receiving the stored answer data by accessing the database server apparatus, and displaying the received answer data.

In the communication system for providing information of a medical doctor's questions to patients, the generating means preferably includes: storing means for storing template question programs corresponding to predetermined answer forms; and program generating means for generating question programs by inserting question sets received from the database server apparatus into the template question programs.

In the communication system for providing information of a medical doctor's questions to patients, the answer forms preferably include at least one of:

(a) a first answer form for answering by selecting at least one among a plurality of selection sentences of answers as an answer to the question; and (b) a second answer form for answering by using a numerical value as an answer to the question.

In the communication system for providing information of a medical doctor's questions to patients, each of the question sets preferably includes data that is indicative of the answer form, and a question sentence.

In the communication system for providing information of a medical doctor's questions to patients, each of the question sets preferably further includes at least one selection sentence.

In the communication system for providing information of a medical doctor's questions to patients, each of the question sets preferably further includes a goal answer entered by a medical doctor.

In the communication system for providing information of a medical doctor's questions to patients, preferably, the patient terminal apparatus further includes storing means for storing entered past answer data, and the displaying means displays stored past answer data in conjunction with the question.

In the communication system for providing information of a medical doctor's questions to patients, the second answer form preferably includes at least one of:

(a) a third answer form for answering by directly entering a numerical value as an answer to the question; and (b) a fourth answer form for answering by entering a numerical value that is indicative of an answer with either one of increasing and decreasing a numerical value starting at an initial value, as an answer to the question.

In the communication system for providing information of a medical doctor's questions to patients, preferably, the terminal apparatus for patient further includes storing means for storing the entered past answer data, and the initial value of the numerical value is a numerical value that is indicative of a previous answer of the corresponding patient included in the stored past answer data.

In the communication system for providing information of a medical doctor's questions to patients, the program generating means preferably includes changing means for changing a display layout of the selection sentences according to at least one of the number of the selection sentences and the length of each selection sentence.

In the communication system for providing information of a medical doctor's questions to patients, the terminal apparatus for medical doctor preferably further includes: transmitting and storing means for entering a remedy policy for a patient, transmitting the entered remedy policy to the database server apparatus, and storing the transmitted remedy policy in the database server apparatus; and further receiving means for receiving the stored remedy policy for the patient by accessing the database server apparatus, and displaying the received remedy policy.

In the communication system for providing information of a medical doctor's questions to patients, the medical doctor terminal apparatus for medical doctor preferably further includes link controlling means for controlling the further receiving means in accordance with a command from an operator so that the further receiving means receives the stored remedy policy for the patient by accessing the database server apparatus and displays the received remedy policy, when the receiving means receives answer data and displays the received answer data.

In the communication system for providing information of a medical doctor's questions to patients, the database server apparatus preferably includes: first storing means for storing information about each of the respective patients; second storing means for storing questions for medical doctor's questions according to the question; third storing means for storing information about linking between respective patients and respective questions; and fourth storing means for storing answer data from the patient terminal apparatus.

In the communication system for providing information of a medical doctor's questions to patients, the third storing means preferably further stores a goal answer entered by a medical doctor, in addition to the information about linking between respective patients and respective questions.

BRIEF DESCRIPTION OF THE DRAWINGS

FIG. 7 is an illustration showing an internal structure of a linking data memory 304c in the hard disk memory 304 shown in FIG. 4;

FIG. 8 is an illustration showing an internal structure of an answer data memory 304d in the hard disk memory 304 shown in FIG. 4;

FIG. 24 is a front view showing a menu screen, showing an example of screen of the medical doctor terminal apparatus 10 shown in FIG. 2;

FIG. 25 is a front view showing a screen of patient registration, showing an example of a screen of the medical doctor terminal apparatus 10 shown in FIG. 2;

FIG. 26 is a front view showing a screen of question set registration, showing an example of a screen of the medical doctor terminal apparatus 10 shown in FIG. 2;

FIG. 27 is a front view showing a screen of answer reading, showing an example of a screen of the medical doctor terminal apparatus 10 shown in FIG. 2;

FIG. 28 is a front view showing a screen of remedy policy entry and reading, showing an example of a screen of the medical doctor terminal apparatus 10 shown in FIG. 2;

FIG. 31 is a front view showing a question screen of an answer form SS3 of a single selection type (single selection from four answers with no goal), showing an example of a screen of the patient terminal apparatus 20 shown in FIG. 3;

FIG. 32 is a front view showing a question screen of an answer form SS4 of a single selection type (single selection from four answers with a goal), showing an example of a screen of the patient terminal apparatus 20 shown in FIG. 3;

FIG. 33 is a front view showing a question screen of an answer form PS1 of a plural selection type (with no goal), showing an example of a screen of the patient terminal apparatus 20 shown in FIG. 3;

FIG. 34 is a front view showing a question screen of an answer form PS2 of a plural selection type (with a goal), showing an example of a screen of the patient terminal apparatus 20 shown in FIG. 3;

FIG. 35 is a front view showing a question screen of an answer form NI1 of a numerical value entry type (with no goal), showing an example of a screen of the patient terminal apparatus 20 shown in FIG. 3;

FIG. 36 is a front view showing a question screen of an answer form NI2 of a numerical value entry type (with a goal), showing an example of a screen of the patient terminal apparatus 20 shown in FIG. 3;

FIG. 37 is a front view showing a question screen of an answer form II1 of an increment or decrement entry type (with no goal), showing an example of a screen of the patient terminal apparatus 20 shown in FIG. 3; and FIG. 38 is a front view showing a question screen of an answer form II2 of an increment or decrement entry type (with a goal), showing an example of a screen of the patient terminal apparatus 20 shown in FIG. 3.

DETAILED DESCRIPTION OF THE PREFERRED EMBODIMENTS

Preferred embodiments according to the present invention will be described below with reference to the attached drawings.

Figure 1:
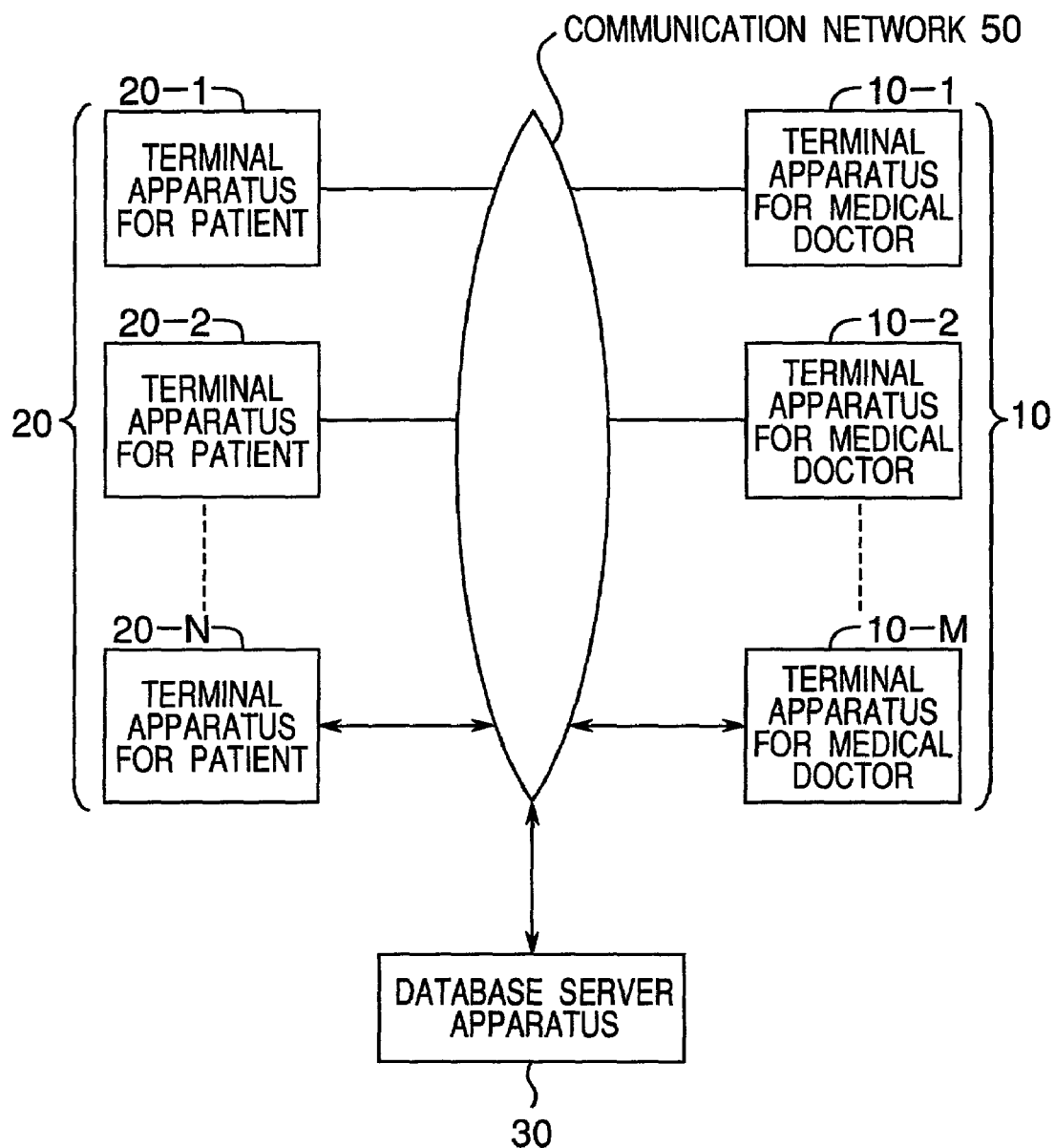
FIG. 1 is a block diagram showing a general configuration of a communication system 1 for providing information of a medical doctor's questions to patients according to a preferred embodiment of the present invention.

FIG. 1 is a block diagram showing a general configuration of a communication system 1 for providing information of a medical doctor's questions to patients according to the preferred embodiment of the present invention.

Referring to FIG. 1, a plurality of terminal apparatuses 10-1 to 10-M for medical doctor(s) (medical doctor terminal apparatuses collectively indicated by reference numeral 10), a plurality of terminal apparatuses 20-1 to 20-N for patient(s) (patient terminal apparatuses collectively indicated by reference numeral 20) and a database server apparatus 30 are connected through a communication network 50 such as a LAN (local area network), a public telephone network or the Internet. The medical doctor terminal apparatuses 10 have the same configuration as each other. For example, each medical doctor terminal apparatus 10 includes a personal computer having a communication facility, and each medical doctor terminal apparatus 10 is configured to execute processing including the registration of patients, the registration of question sets for a medical doctor's questions to patients, the reading of answers, and the entry and reading of remedy policies. The patient terminal apparatuses 20 have the same configuration as each other. For example, each patient terminal apparatus 20 includes a personal computer having a communication facility, and each patient terminal apparatus 20 is configured to generate question programs in accordance with the question sets transmitted from each medical doctor terminal apparatus 10 through the database server apparatus 30 and store the generated question programs, and to perform a process for the patient terminal, which executes the stored question programs so as to display questions to each patient in conjunction with previous answer data, store answer data from each patient, and transmit the stored answer data to the database sewer apparatus 30. For example, the database server apparatus 30 includes a computer having a communication facility, and the database sewer apparatus 30 is configured to transmit and receive question data for a medical doctor's questions to patients, answer data, remedy policy data and the like between each medical doctor terminal apparatus 10 and each patient terminal apparatus 20, and to store these data.

In the preferred embodiment, the communication system 1 for providing information of a medical doctor's questions to patients includes the medical doctor terminal apparatuses 10, the patient terminal apparatuses 20, and the database server apparatus 30 which stores the question sets for the medical doctor's questions to patients, and the apparatuses 10, 20, 30 are connected through the communication network 50. More specifically, each patient terminal apparatus 20 generates the question programs for a medical doctor's questions to patients in accordance with the question sets received from the database server apparatus 30, and executes the generated question programs so as to display questions for the medical doctor's questions to patients, enter answer data to the displayed questions, and transmit the entered answer data to the database server apparatus 30, which then stores the transmitted answer data. Each medical doctor terminal apparatus 10 accesses the database server apparatus 30 so as to receive the stored answer data and display the received answer data.

Figure 2:
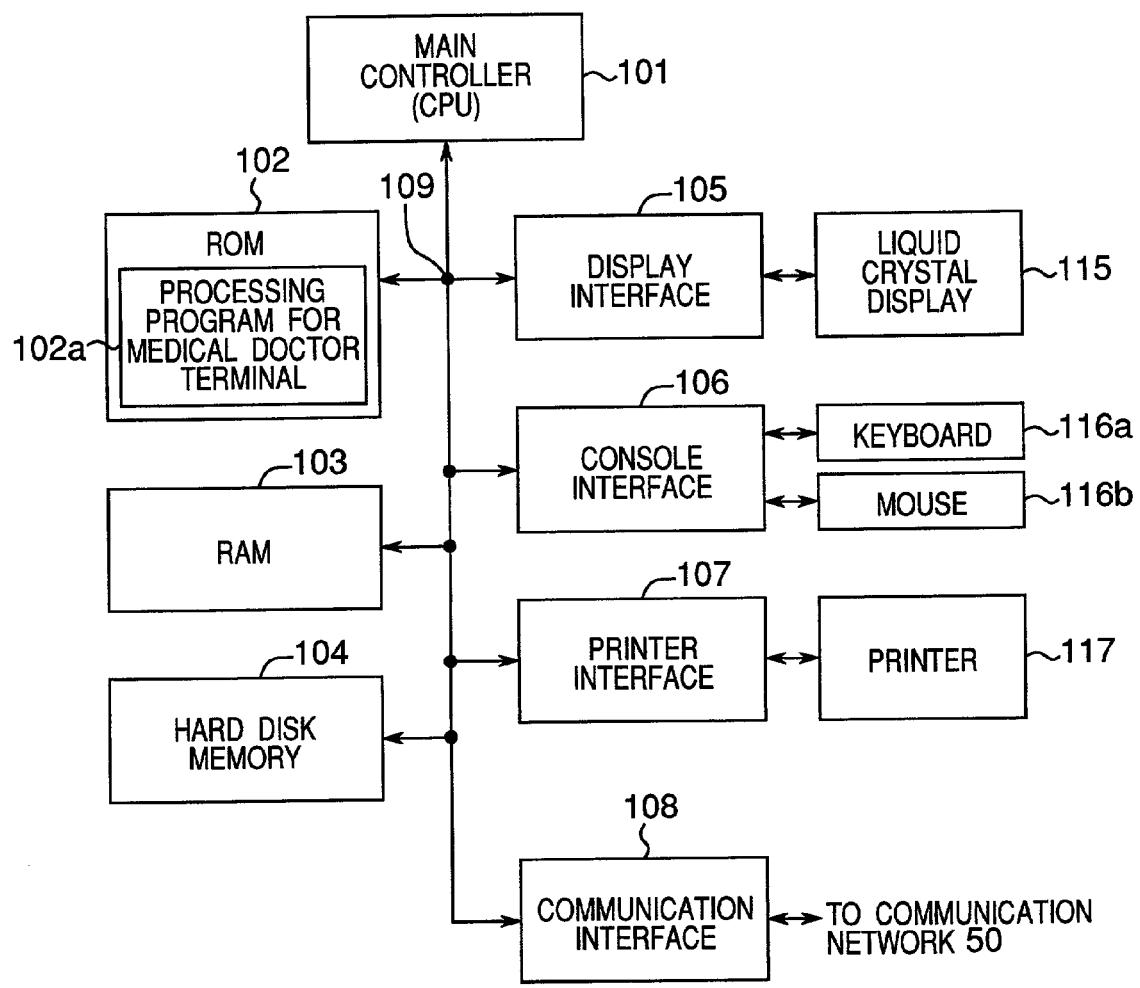
FIG. 2 is a block diagram showing a configuration of each medical doctor terminal apparatus 10 shown in FIG. 1.

FIG. 2 is a block diagram showing a configuration of each medical doctor terminal apparatus 10 shown in FIG. 1.

Referring to FIG. 2, each medical doctor terminal apparatus 10 includes:

(a) a main controller (CPU (Central Processing Unit)) 101 of a personal computer, which performs and controls the operation and processing of the medical doctor terminal apparatus 10;

(b) a ROM (Read Only Memory) 102 which stores operation programs, basic programs such as a medical doctor terminal processing program 102a for a process for medical doctor terminal as shown in FIGS. 10 to 14, and data required for executing the programs;

(c) a RAM (Random Access Memory) 103 which operates as a working memory of the main controller 101 so as to temporarily store parameters and data required for the process for the medical doctor terminal;

(d) a hard disk memory 104 which stores application programs and various data;

(e) a display interface 105 which is connected to a liquid crystal display 115 for displaying data, screens and the like processed by the main controller 101 so as to convert image data to be displayed into an image signal for the liquid crystal display 115 and output the image signal to the liquid crystal display 115, which then displays the image data;

(f) an operating section interface or console interface 106 which is connected to a keyboard 116a for entering predetermined data and commands and a mouse 116b for entering commands on the liquid crystal display 115 so as to receive data and commands entered through the keyboard 116a or the mouse 116b, perform an interface process such as predetermined signal conversion on the received data, and transmit the processed data to the main controller 101;

(g) a printer interface 107 which is connected to a printer 117 for printing data and the like processed by the main controller 101 so as to perform a process such as predetermined signal conversion on print data to be printed and output the processed data to the printer 117, which then prints the output data; and (h) a communication interface 108 which is connected to the database server apparatus 30 through the communication network 50 so as to transmit and receive data to and from the database server apparatus 30.

In this case, these circuits 101 to 108 are connected through a bus 109.

For example, when a LAN is used as the communication network 50, a LAN interface is used as the communication interface 108. Alternatively, when a public telephone network, for example, is used as the communication network 50, a modem is used as the communication interface 108. Alternatively, when the Internet, for example, is used as the communication network 50, a router including a DSU (Digital Service Unit) is used as the communication interface 108.

Figure 3:
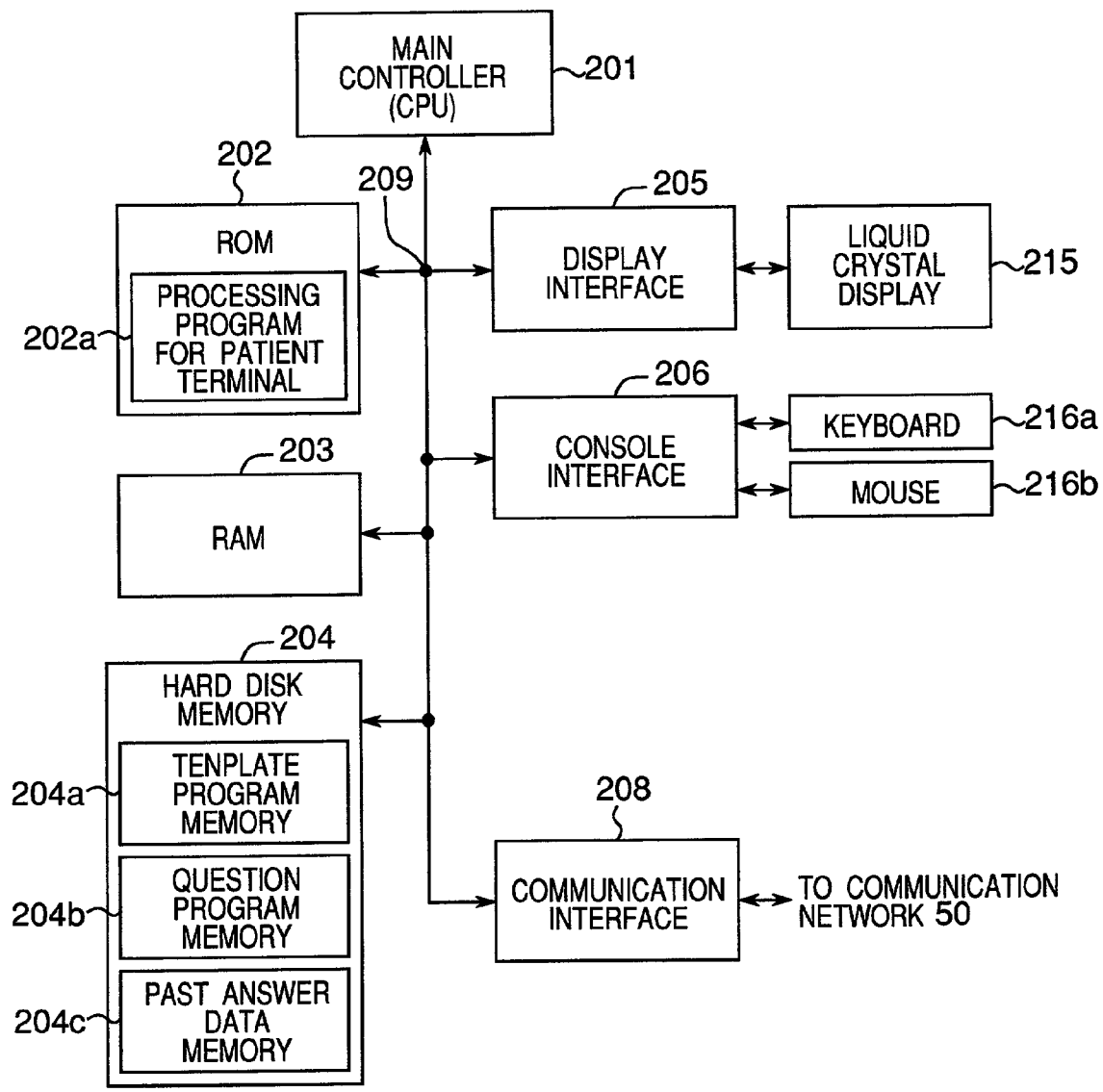
FIG. 3 is a block diagram showing a configuration of each patient terminal apparatus 20 shown in FIG. 1.

FIG. 3 is a block diagram showing a configuration of each patient terminal apparatus 20 shown in FIG. 1.

Referring to FIG. 3, each patient terminal apparatus 20 includes:

(a) a main controller (CPU (Central Processing Unit)) 201 of a personal computer, which performs and controls the operation and processing of the patient terminal apparatus 20;

(b) a ROM (Read Only Memory) 202 which stores operation programs, basic programs such as a patient terminal processing program 202a a process for the patient terminal as shown in FIGS. 15 to 19, and data required for executing the programs;

(c) a RAM (Random Access Memory) 203 which operates as a working memory of the main controller 201 so as to temporarily store parameters and data required for the process for the patient terminal;

(d) a hard disk memory 204 which stores application programs and various data, and in particular, includes a template program memory 204a for storing four types of template question programs (hereinafter referred to as template programs), each of which functions as a template for generating question programs for a medical doctor's questions to patients, a question program memory 204b for storing the question programs generated by the terminal apparatus 20 for patient, and a past answer data memory 204c for storing past answer data to questions;

(e) a display interface 205 which is connected to a liquid crystal display 215 for displaying data, screens and the like processed by the main controller 201 so as to convert image data to be displayed into an image signal for the liquid crystal display 215 and output the image signal to the liquid crystal display 215, which then displays the image data;

(f) an operating section interface or a console interface 206 which is connected to a keyboard 216a for entering predetermined data and commands and a mouse 216b for entering commands on the liquid crystal display 215 so as to receive data and commands entered through the keyboard 216a or the mouse 216b, perform an interface process such as predetermined signal conversion on the received data, and transmit the processed data to the main controller 201; and (g) a communication interface 208 which is a circuit apparatus similar to the communication interface 108, and is connected to the database server apparatus 30 through the communication network 50 so as to transmit and receive data to and from the database server apparatus 30.

In this case, these circuits 201, 202, 203, 204, 205, 206 and 208 are connected through a bus 209.

Figure 4:
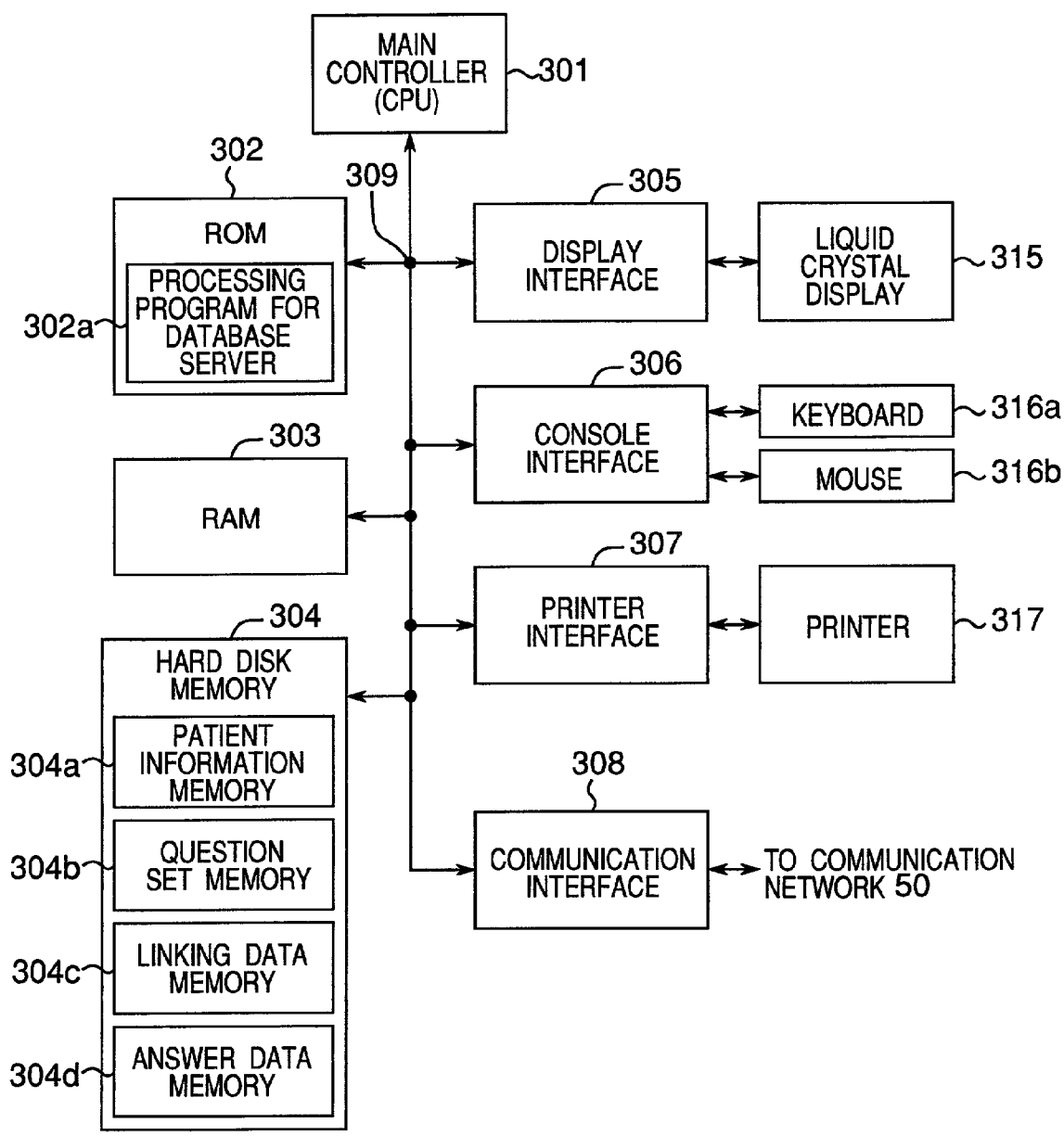
FIG. 4 is a block diagram showing a configuration of a database server apparatus 30 shown in FIG. 1.

FIG. 4 is a block diagram showing a configuration of the database server apparatus 30 shown in FIG. 1.

Figure 5:
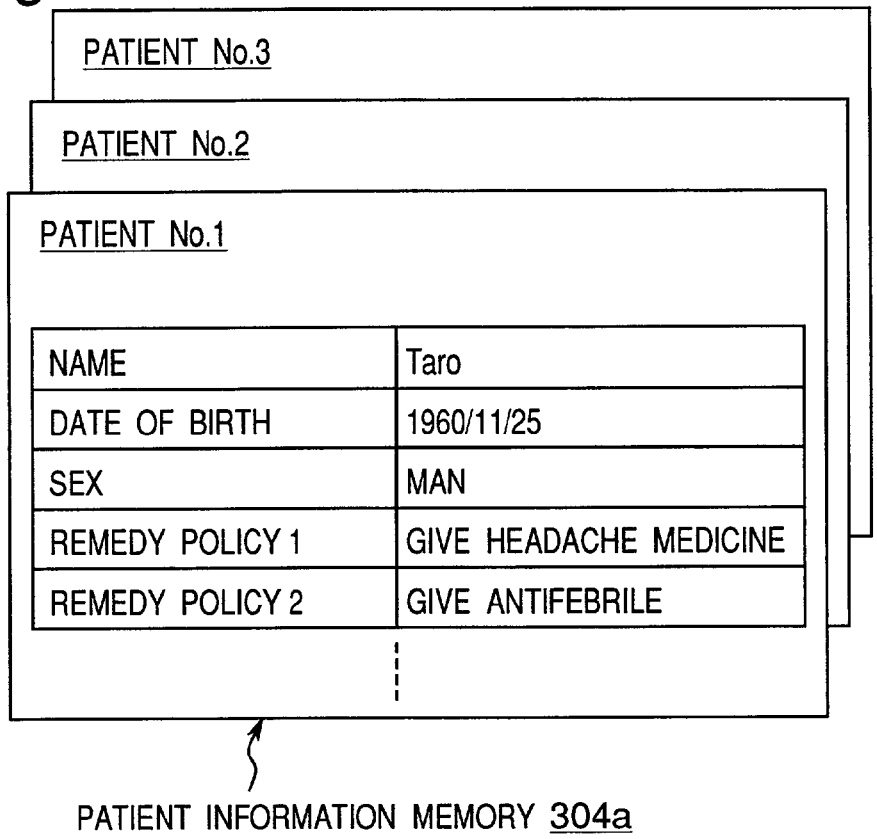
FIG. 5 is an illustration showing an internal structure of a patient information memory 304a in a hard disk memory 304 shown in FIG. 4.
Figure 6:
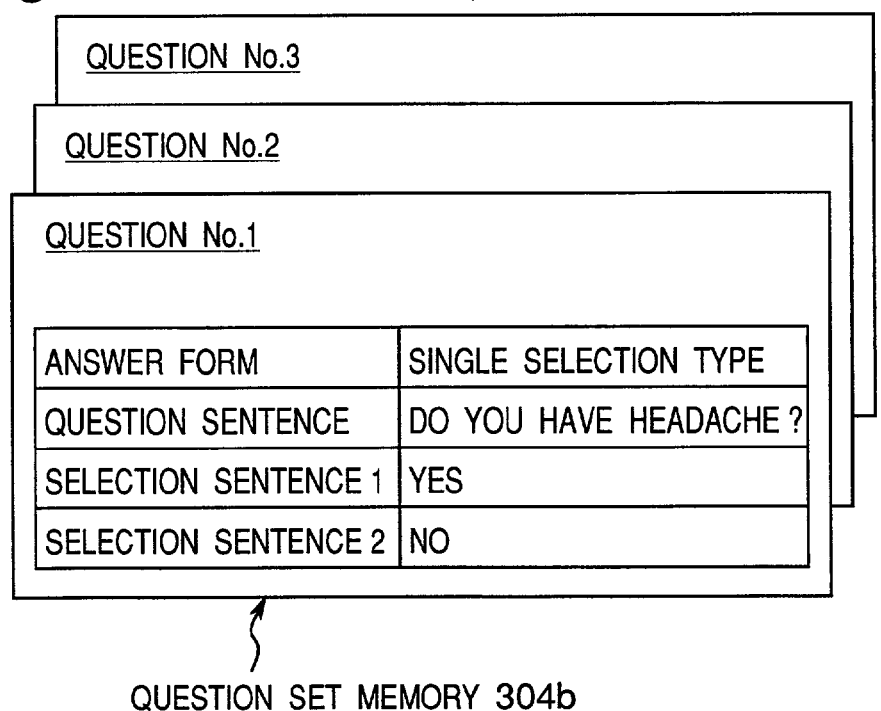
FIG. 6 is an illustration showing an internal structure of a question set memory 304b in the hard disk memory 304 shown in FIG. 4.

Referring to FIG. 4, the database server apparatus 30 includes:

(a) a main controller (CPU (Central Processing Unit)) 301 of a computer, which performs and controls the operation and processing of the database server apparatus 30;

(b) a ROM (Read Only Memory) 302 which stores operation programs, basic programs such as a database server processing program 302a for a process for the database server as shown in FIGS. 20 to 23, and data required for executing the programs;

(c) a RAM (Random Access Memory) 303 which operates as a working memory of the main controller 301 so as to temporarily store parameters and data required for the process for the database server;

(d) a hard disk memory 304 which stores application programs and various data, and in particular, includes: a patient information memory 304a for storing patient information and having an internal structure as shown in FIG. 5; a question set memory 304b for storing question sets and having an internal structure as shown in FIG. 6; a linking data memory 304c for storing linking data and having an internal structure as shown in FIG. 7; and an answer data memory 304d for storing answer data and having an internal structure as shown in FIG. 8;

(e) a display interface 305 which is connected to a liquid crystal display 315 for displaying data, screens and the like processed by the main controller 301 so as to convert image data to be displayed into an image signal for the liquid crystal display 315 and output the image signal to the liquid crystal display 315, which then displays the image data;

(f) an operating section interface or console interface 306 which is connected to a keyboard 316a for entering predetermined data and commands and a mouse 316b for entering commands on the liquid crystal display 315 so as to receive data and commands entered through the keyboard 316a or the mouse 316b, perform an interface process such as predetermined signal conversion on the received data, and transmit the processed data to the main controller 301;

(g) a printer interface 307 which is connected to a printer 317 for printing data and the like processed by the main controller 301 so as to perform a process such as predetermined signal conversion on print data to be printed and output the processed data to the printer 317, which then prints the output data; and (h) a communication interface 308 which is the same circuit as the communication interfaces 108 and 208, and is connected to the medical doctor terminal apparatus 10 and the patient terminal apparatus 20 through the communication network 50 so as to transmit and receive data to and from the medical doctor terminal apparatus 10 and the patient terminal apparatus 20.

In this case, these circuits 301 to 308 are connected through a bus 309.

FIG. 5 is an illustration showing an internal structure of the patient information memory 304a in the hard disk memory 304 shown in FIG. 4. Referring to FIG. 5, patient data stored in the patient information memory 304a is divided into individual patient parts for each respective patient identified by the respective patient numbers, and patient data of each patient includes the following items:

(a) the name of patient;
(b) the date of birth of patient;

(c) the sex of patient; and (d) the remedy policy or policies of medical doctor for patient.

Figure 11:
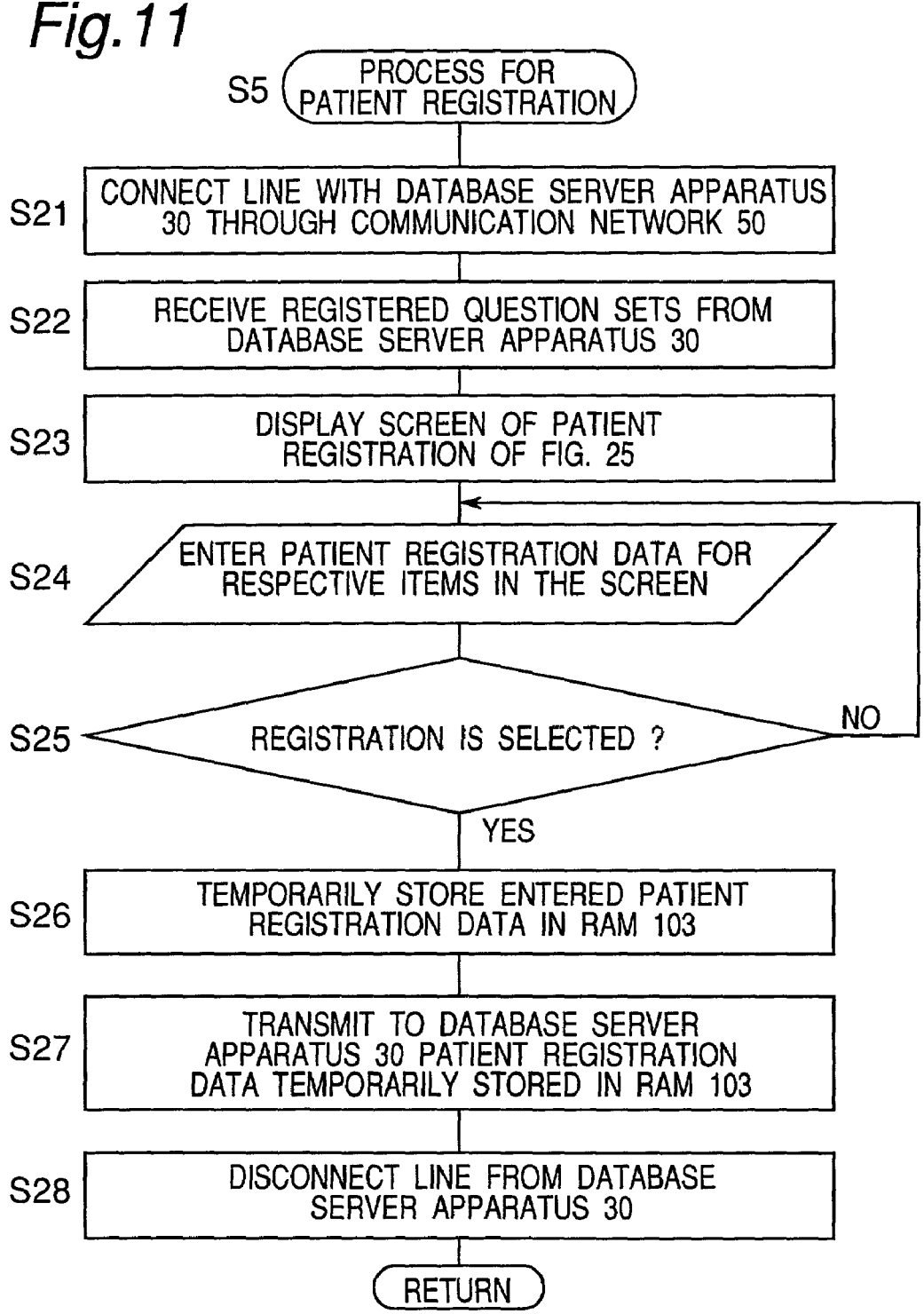
FIG. 11 is a flowchart illustrating a process for patient registration (step S5) which is a subroutine of the process illustrated in FIG. 10.
Figure 14:
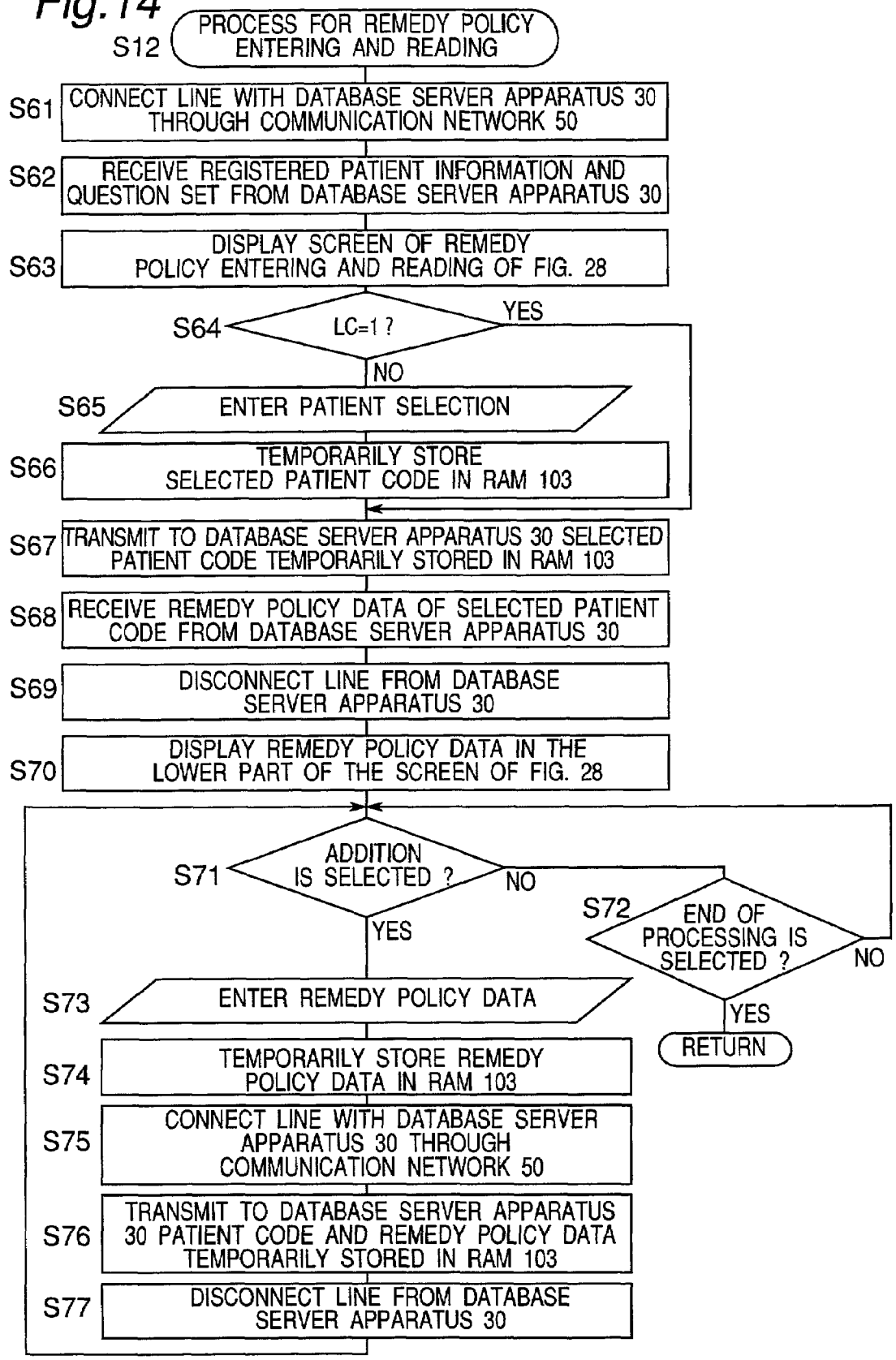
FIG. 14 is a flowchart illustrating a process for remedy policy entering and reading (step S12) which is a subroutine of the process illustrated in FIG. 10.

The patient information illustrated in FIG. 5, exclusive of the remedy policy or policies, is entered by a medical doctor using the medical doctor terminal apparatus 10 in a process for patient registration illustrated in FIG. 11. Then, the patient information is transferred to the database server apparatus 30, which then stores the patient information. The remedy policy or policies are entered by the medical doctor using the medical doctor terminal apparatus in a process for remedy policy entering and reading as illustrated in FIG. 14. Thereafter, the remedy policy or policies are transferred to the database server apparatus 30, which then stores the remedy policy or policies.

FIG. 6 is an illustration showing an internal structure of the question set memory 304b in the hard disk memory 304 shown in FIG. 4. Referring to FIG. 6, question set data stored in the question set memory 304b is divided into individual question parts for each respective question identified by the respective question numbers, and data of each question includes the following items:

(a) an answer form;

(b) a question sentence; and (c) selection sentences (it should be noted that there is no selection sentence when the answer form is of a numerical value entry type).

In the preferred embodiment, the answer forms include the following ten types of answer forms illustrated as examples of screens in FIGS. 29 to 38.

Figure 29:
FIG. 29 is a front view showing a question screen of an answer form SS1 of a single selection type (single selection from two answers with no goal), showing an example of a screen of the patient terminal apparatus 20 shown in FIG. 3.

(a) An answer form SS1 of a single selection type (single selection from two answers with no goal). As illustrated in FIG. 29, this is the answer form of a single selection from two answers, which is adapted to have no goal and to make an answer to a question in the following manner: for example, a patient clicks the mouse 216b on either one of an answer example 224 of a selection sentence saying YES and an answer example 224 of a selection sentence saying NO, and then clicks on OK 225.

Figure 30:
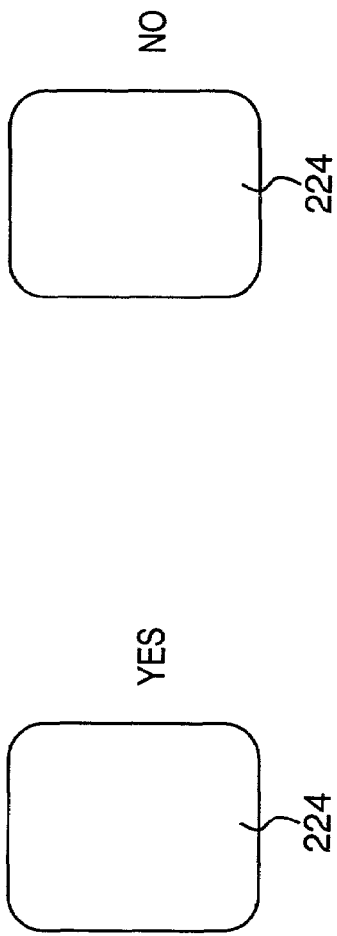
FIG. 30 is a front view showing a question screen of an answer form SS2 of a single selection type (single selection from two answers with a goal), showing an example of a screen of the patient terminal apparatus 20 shown in FIG. 3.

(b) An answer form SS2 of a single selection type (single selection from two answers with a goal). As illustrated in FIG. 30, this is the answer form of a single selection from two answers, which is adapted to have a goal and to make an answer to a question in the following manner: for example, a patient clicks the mouse 216b on either one of the answer example 224 of the selection sentence saying YES and the answer example 224 of the selection sentence saying NO with reference to the displayed goal, and then clicks on the OK 225.

(c) An answer form SS3 of a single selection type (single selection from four answers with no goal). As illustrated in FIG. 31, this is the answer form of a single selection from four answers, which is adapted to have no goal and to make an answer to a question in the following manner: for example, a patient clicks the mouse 216b on the selected one of answer examples 224 of four selection sentences, and then clicks on the OK 225.

(d) An answer form SS4 of a single selection type (single selection from four answers with a goal). As illustrated in FIG. 32, this is the answer form of a single selection from four answers, which is adapted to have a goal and to make an answer to a question in the following manner: for example, a patient clicks the mouse 216b on the selected one of answer examples 224 of four selection sentences with reference to the displayed goal, and then clicks on the OK 225.

(e) An answer form PS1 of a plural selection type (with no goal). As illustrated in FIG. 33, this is the answer form capable of making a plurality of answers, which is adapted to have no goal and to make an answer or answers to a question in the following manner: for example, a patient clicks the mouse 216b on the selected one or more of answer examples of a plurality of selection sentences such as four answer examples 224, and then clicks on the OK 225.

(f) An answer form PS2 of a plural selection type (with a goal). As illustrated in FIG. 34, this is the answer form capable of making a plurality of answers, which is adapted to have a goal and to make an answer or answers to a question in the following manner: for example, a patient clicks the mouse 216b on the selected one or more of answer examples of a plurality of selection sentences such as six answer examples 224 with reference to the displayed goal, and then clicks on the OK 225.

(g) An answer form NI1 of a numerical value entry type (with no goal). As illustrated in FIG. 35, this is the answer form which is adapted to have no goal and to make an answer to a question in the following manner: a patient directly enters a numerical value that is indicative of an answer in a numerical value display 221 by clicking the mouse 216b on ten numeric keys 222 on an image, and then clicks on OK 223.

(h) An answer form NI2 of a numerical value entry type (with a goal). As illustrated in FIG. 36, this is the answer form which is adapted to have a goal and to make an answer to a question in the following manner: a patient directly enters a numerical value that is indicative of an answer in the numerical value display 221 by clicking the mouse 216b on the numeric keys 222 on an image with reference to the displayed goal, and then clicks on the OK 223.

(i) An answer form II1 of a numerical value entry type (with no goal). As illustrated in FIG. 37, this is the answer form which is adapted to have no goal and to make an answer to a question in the following manner: a patient enters a numerical value that is indicative of an answer in a numerical value display 231 by means of an answer form of an increment or decrement entry type, and then clicks on OK 234. More specifically, the answer form of an increment or decrement entry type means that a previous numerical value displayed in the numerical value display 231 is incremented or decremented by clicking the mouse 216b on either one of an increment operating section and increment button 232 to increment the numerical value by one with one click of the mouse 216b or a decrement operating section or decrement button 233 to decrement the numerical value by one with one click of the mouse 216b.

(j) An answer form II2 of a numerical value entry type (with a goal). As illustrated in FIG. 38, this is the answer form which is adapted to have a goal and to make an answer to a question in the following manner: a patient enters a numerical value that is indicative of an answer in the numerical value display 231 by means of the answer form of the increment or decrement entry type with reference to the displayed goal, and then clicks on the OK 234. More specifically, the answer form of the increment or decrement entry type means that a previous numerical value displayed in the numerical value display 231 is incremented or decremented by clicking the mouse 216b on either one of the increment button 232 to increment the numerical value by one with one click of the mouse 216b and the decrement button 233 to decrement the numerical value by one with one click of the mouse 216b.

In the preferred embodiment, the answer forms include the above-described ten types of answer forms, and therefore, a patient can make answers to various questions. Selection sentences are displayed for each of a number of questions, and therefore, a patient can select an appropriate sentence or sentences to answer each question, which makes it very easy for a patient to answer the questions. Moreover, a past answer such as a previous answer is displayed for each of a number of questions, which therefore facilitates answering each question with reference to the past answer. Furthermore, a goal is displayed for each of a number questions, and therefore, a patient can make an effort to achieve improvement of his or her life and so on with a sense of purpose of accomplishing his or her goal, so that the patient can be quickly cured of a disease. In addition, a patient can enter a current numerical value by increasing or decreasing a numerical value starting at an initial value, e.g., a numerical value that is indicative of a previous answer, and therefore, the entry of numerical value is very simple, so that the operationality can be greatly improved.

Figure 9:
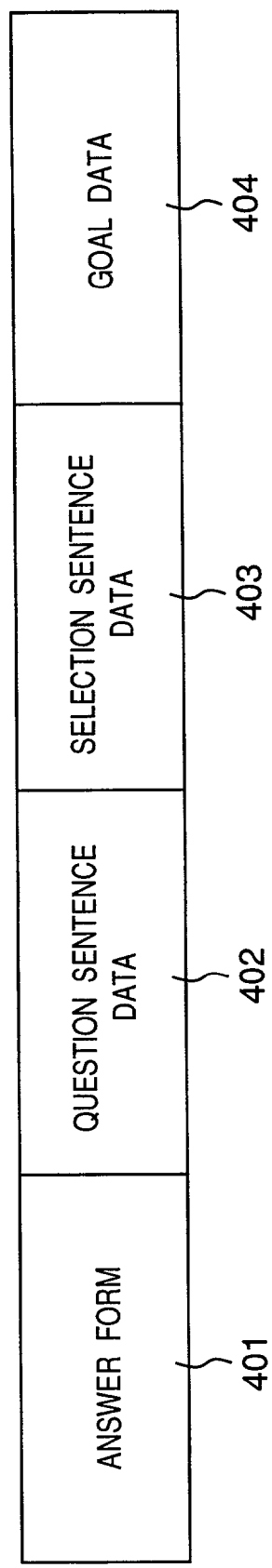
FIG. 9 is an illustration showing a data format of a question set which is transmitted from the database server apparatus 30 shown in FIG. 1 to the patient terminal apparatus 20.
Figure 12:
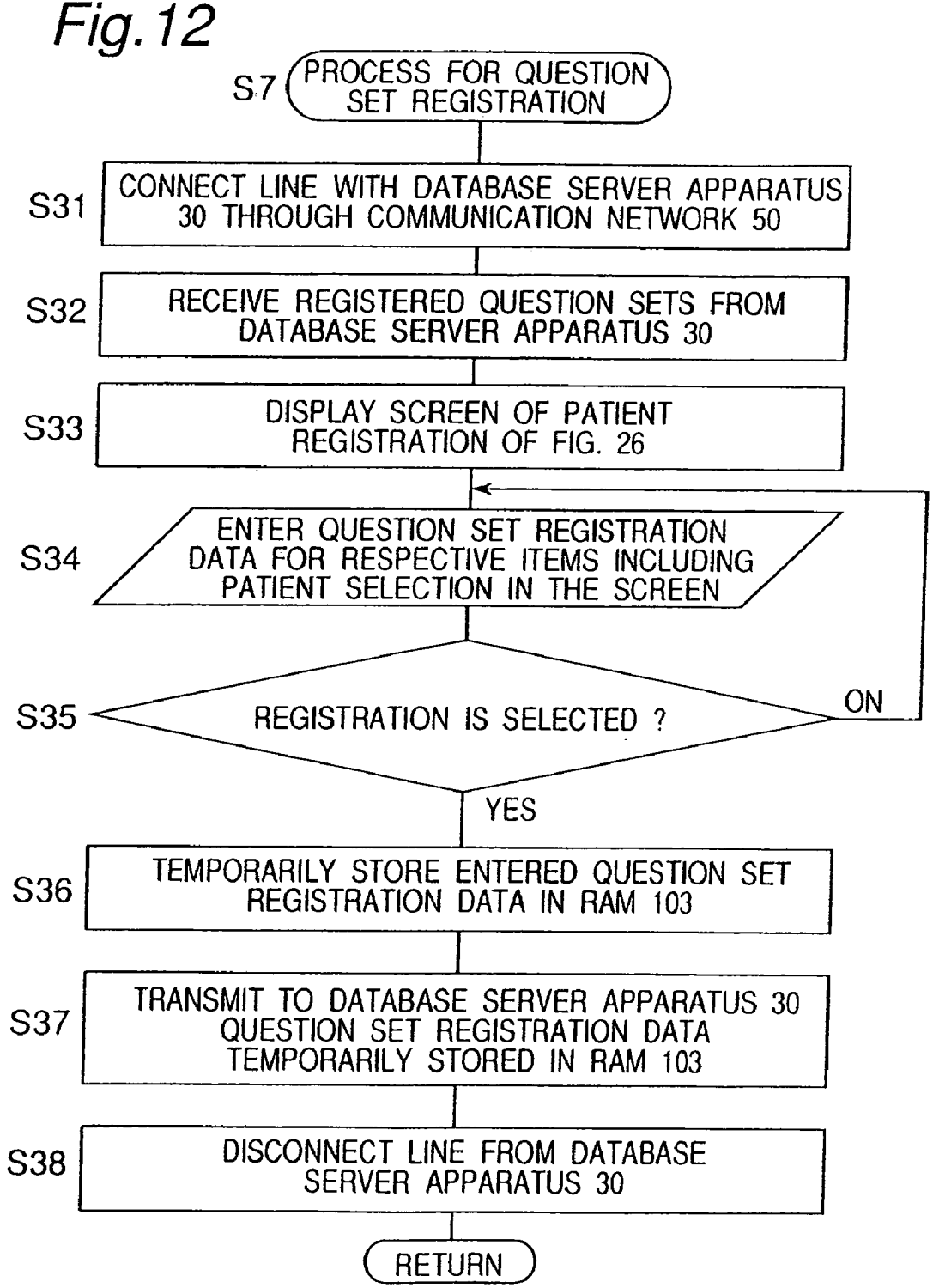
FIG. 12 is a flowchart illustrating a process for question set registration (step S7) which is a subroutine of the process illustrated in FIG. 10.

The above-mentioned question data is entered by a medical doctor using the medical doctor terminal apparatus 10 in a process for question set registration illustrated in FIG. 12, and thereafter, the question data is transferred to the database server apparatus 30, which then stores the question data. As shown in FIG. 9, the question set includes an answer form 401, question sentence data 402, selection sentence data 403 (which is blank data when the answer form is of the numerical value entry type), and goal data 404 (which is blank data when the answer form is of the no-goal type).

FIG. 7 is an illustration showing an internal structure of the linking data memory 304c in the hard disk memory 304 shown in FIG. 4.

Referring to FIG. 7, the linking data stored in the linking data memory 304c has a tabular form in which patients identified by their respective patient numbers are arranged in a column direction and questions identified by their question numbers are arranged in a row direction, and the presence or absence of a circle in the intersection of the column of each patient and the row of each question indicates whether or not each question is already put to each patient. Goal data is stored when there is a goal that a medical doctor sets for a question corresponding to an intersection with a circle. Storage of such linking data eliminates the need to treat questions as questions unique to the patients, thus making the questions applicable to all the patients, and therefore, permits a system having a very high degree of general versatility to be provided.

Accordingly, linkage between each patient and each question, more specifically, whether or not a given question is specified for a given patient, in conjunction with a goal if it is set for the question, is stored as the linking data shown in FIG. 7. The above-mentioned linking data is entered by a medical doctor using the medical doctor terminal apparatus 10 in the process for question set registration illustrated in FIG. 12. Thereafter, the linking data is transferred to the database server apparatus 30, which then stores the linking data in a process of step S245 shown in FIG. 21.

FIG. 8 is an illustration showing an internal structure of the answer data memory 304d in the hard disk memory 304 shown in FIG. 4.

Referring to FIG. 8, the answer data is stored in tabular form, which includes the date and time of answer, a patient code indicated by the patient number, the question number, the goal, and the answer. The above-mentioned answer data is entered by a patient using the patient terminal apparatus 20 in the process for the patient terminal shown in FIGS. 15 and 16, and thereafter, the answer data is transferred to the database server apparatus 30, which then stores the answer data.

The communication system 1 for providing information of a medical doctor's questions to patients shown in FIG. 1 having the above-described configuration is designed to transmit and receive a signal and data between the medical doctor terminal apparatus 10 and the database server apparatus 30 and to transmit and receive a signal and data between the patient terminal apparatus 20 and the database server apparatus 30, as described in detail below. The signal and data may be encrypted and decrypted by a transmitting apparatus and a receiving apparatus, respectively, for the purpose of communicating the signal and data.

Figure 10:
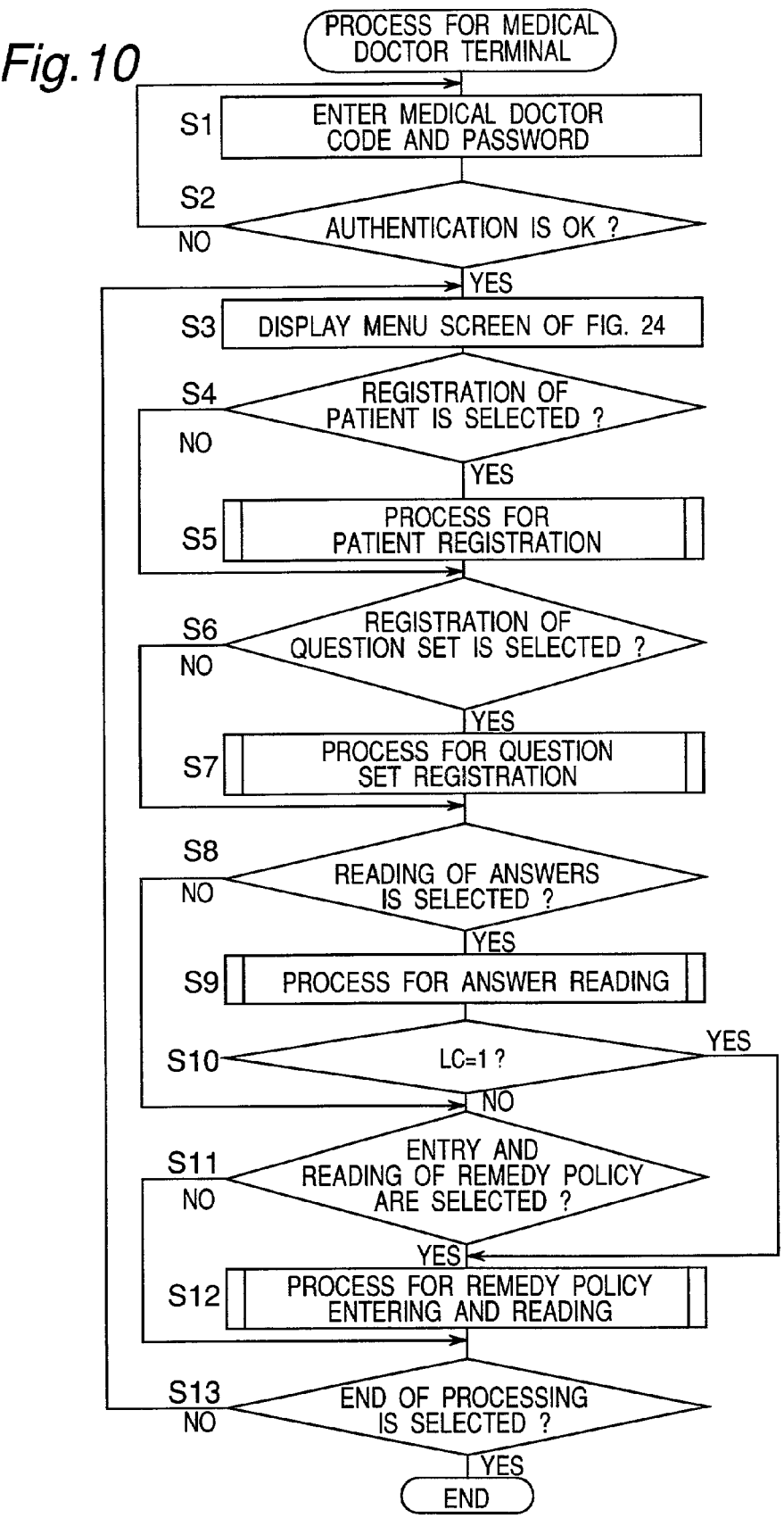
FIG. 10 is a flowchart illustrating a process for a medical doctor terminal, which is performed by a main controller 101 of the medical doctor terminal apparatus 10 shown in FIG. 2.

FIG. 10 is a flowchart illustrating the process for the medical doctor terminal, which is executed by the main controller 101 of the medical doctor terminal apparatus 10 shown in FIG. 2. In the process for the medical doctor terminal, "entry" means that a medical doctor enters data or a numerical value by using the keyboard 116a or the mouse 116b shown in FIG. 2. "Display" means that image data from the main controller 101 shown in FIG. 2 is outputted to the liquid crystal display 115 through the display interface 105 and the output image data is displayed on the liquid crystal display 115.

In step S1 shown in FIG. 10, a medical doctor code and a password are entered first. Then, in step S2, a judgment is made as to whether or not authentication is OK, that is, whether or not the entered medical doctor code and password data match authentication data previously entered and registered, and the process flow returns to step S1 if authentication is not OK (NO), or the process flow proceeds to step S3 if authentication is OK (YES). Then, in step S3, a menu screen of FIG. 24 having the following alternatives is displayed, and a medical doctor who is an operator chooses one of these alternatives and clicks the mouse 116b on the chosen alternative so as to select a process. The alternatives are as follows:

(a) the registration of patient;
(b) the registration of a question set;
(c) the reading of answers;
(d) the entry and reading of a remedy policy; and
(e) the end of processing.

Figure 13:
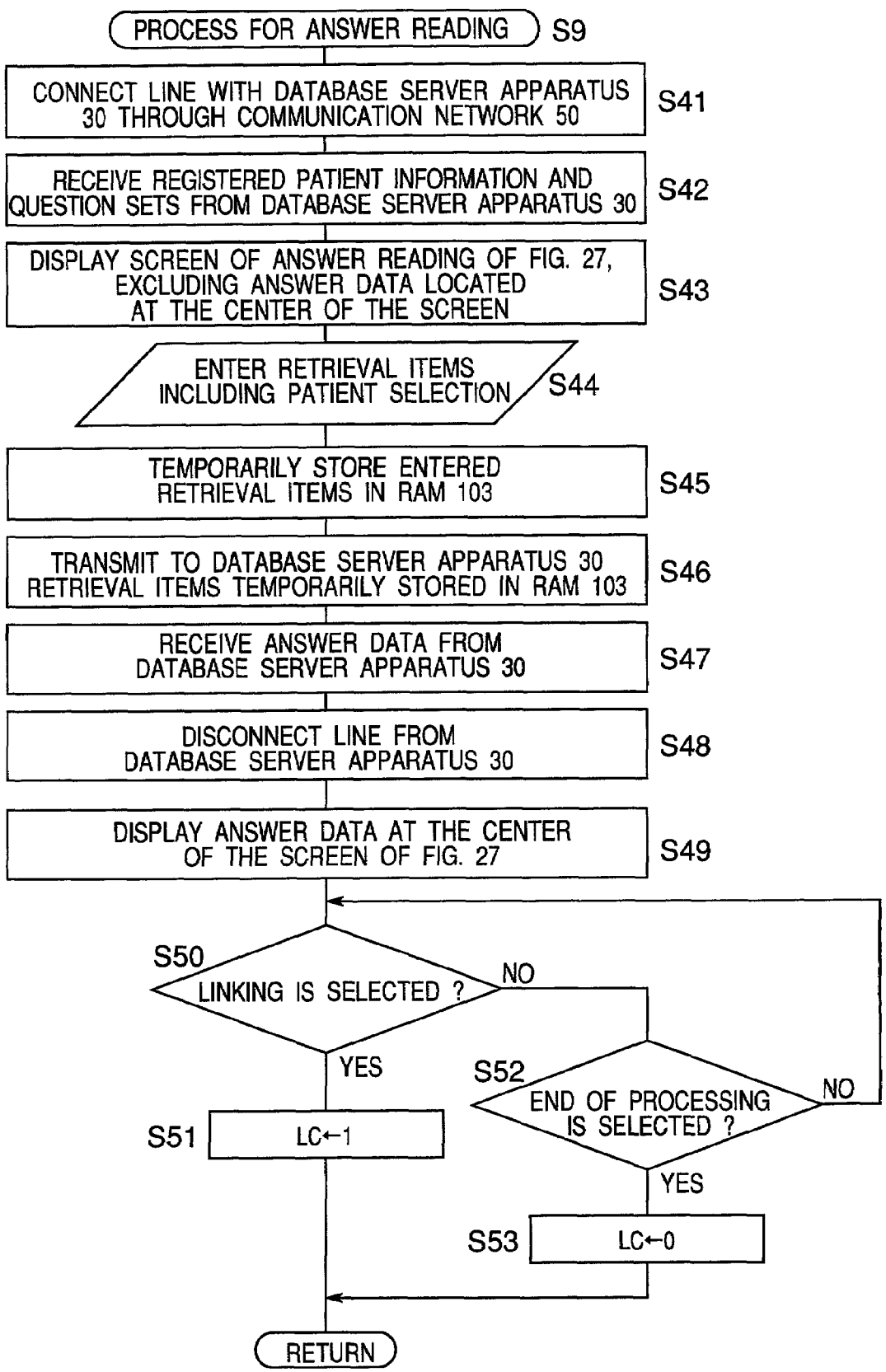
FIG. 13 is a flowchart illustrating a process for answer reading (step S9) which is a subroutine of the process illustrated in FIG. 10.

In step S4, a judgment is made as to whether or not the registration of patient is selected. If the registration of patient is selected (YES), the process flow proceeds to step S5, where the process for patient registration illustrated in FIG. 11 is performed, and thereafter, the process flow proceeds to step S6. If the registration of patient is not selected in step S4 (NO), the process flow proceeds directly to step S6. Then, in step S6, a judgment is made as to whether or not the registration of a question set is selected. If the registration of a question set is selected (YES), the process flow proceeds to step S7. In step S7, the process for question set registration illustrated in FIG. 12 is performed, and thereafter, the process flow proceeds to step S8. If the registration of a question set is not selected in step S6 (NO), the process flow proceeds directly to step S8. Then, in step S8, a judgment is made as to whether or not the reading of answers is selected. If the reading of answers is selected (YES), the process flow proceeds to step S9, where a process for answer reading illustrated in FIG. 13 is performed, and thereafter, the process flow proceeds to step S10. If the reading of answers is not selected in step S8 (NO), the process flow proceeds directly to step S11. In step S10, a judgment is made as to whether or not a link code LC is equal to 1, namely, the link code LC indicates whether or not a command is given to link to the entry of a remedy policy in the process for answer reading illustrated in FIG. 13 in order to jump directly to step S12 of the process for remedy policy entering and reading in conjunction with the patient code indicated by the patient number. That is, a judgment is made as to whether or not the above-mentioned command to jump is given. The process flow jumps to step S12 if the command is given (YES), or the process flow proceeds to step S11 if the command is not given (NO). Then, in step S11, a judgment is made as to whether or not the entry and reading of remedy policy is selected. If the entry and reading of a remedy policy is selected (YES), the process flow proceeds to step S12, where the process for remedy policy entering and reading illustrated in FIG. 14 is performed, and thereafter, the process flow proceeds to step S13. If the entry and reading of remedy policy is not selected in step S11 (NO), the process flow proceeds directly to step S13. Then, in step S13, a judgment is made as to whether or not the end of processing is selected, and the process flow returns to step S3 if the end of processing is not selected (NO), or the process for medical doctor terminal is ended if the end of processing is selected (YES).

FIG. 11 is a flowchart illustrating the process for patient registration (step S5) which is a subroutine of the process illustrated in FIG. 10.

In step S21 illustrated in FIG. 11, a line is first connected with the database server apparatus 30 through the communication network 50. In step S22, question sets registered in the question set memory 304b of the database server apparatus 30 are received. Then, in step S23, a screen of patient registration shown in FIG. 25 is displayed. In step S24, a medical doctor uses the keyboard 116a to enter patient data for items in the screen, which include the patient code indicated by the patient number, the name of a patient, the date of birth of a patient and the sex of a patient which are displayed in an upper part of the screen, as shown as an example of screen in FIG. 25. Question sentences of question sets already registered in the question set memory 304b of the database server apparatus 30 are displayed in a lower part of the screen, and thus, the medical doctor clicks the mouse 116b on the second column from the left, so that circles appear so as to link necessary questions with a patient to be registered. As needed, the medical doctor enters a goal of the patient to be registered for a question. After the above-mentioned entry, the medical doctor clicks the mouse 116b on a registration button located in the bottom part of the screen (YES in step S25), and thus, the process flow proceeds to step S26. If NO in step S25, the process flow returns to step S24. Then, in step S26, the entered patient registration data is temporarily stored in the RAM 103. In step S27, the patient registration data temporarily stored in the RAM 103 is transmitted to the database server apparatus 30. In step S28, the line is disconnected from the database server apparatus 30, and thus, the process flow returns to the original main routine.

FIG. 12 is a flowchart illustrating the process for question set registration (step S7) which is a subroutine of the process illustrated in FIG. 10.

In step S31 illustrated in FIG. 12, a line is first connected with the database server apparatus 30 through the communication network 50. In step S32, patient information registered in the patient information memory 304a of the database server apparatus 30 is received. Then, in step S33, a screen of a question set registration shown in FIG. 26 is displayed. In step S34, a medical doctor enters question set registration data for items in the screen, which include patient selection. The medical doctor uses the keyboard 116a or the mouse 116b to enter the patient number, the selection of answer form, the question sentence, and the selection sentences of answer examples (it should be noted that there is no selection sentence when the answer form is of a numerical value entry type), which are displayed in an upper part of the screen. The names of patients of the patient information are displayed in a lower part of the screen, and thus, the medical doctor clicks the mouse 116b on all patients to be linked and thus selects the patients in order to link an additional question set to be registered with the patients who need the question set. When a patient is selected, a circle followed by the name of the patient is reversed from white to black. Then, in step S35, a judgment is made as to whether or not the registration is selected, and the process flow returns to step S34 if the registration is not selected (NO), or the process flow proceeds to step S36 if the registration is selected (YES). In step S36, the entered question set registration data is temporarily stored in the RAM 103. In step S37, the question set registration data temporarily stored in the RAM 103 is transmitted to the database server apparatus 30. In step S38, the line is disconnected from the database server apparatus 30, and thus, the process flow returns to the original main routine.

FIG. 13 is a flowchart illustrating the process for answer reading (step S9) which is a subroutine of the process illustrated in FIG. 10.

In step S41 illustrated in FIG. 13, a line is first connected with the database server apparatus 30 through the communication network 50. In step S42, the patient information registered in the patient information memory 304a of the database server apparatus 30 and the question sets registered in the question set memory 304b thereof are received. Then, in step S43, a screen of answer reading shown in FIG. 27 is displayed (it should be noted that an answer data portion in a center part of FIG. 27 is not displayed at this time). In step S44, a medical doctor enters a retrieval item including patient selection. For this entry, the patient selection is first performed by clicking the mouse 116b on a circle on the left side of the name of the selected one of a plurality of patients displayed in the patient selection. Then, to further narrow a search, the medical doctor clicks on either "retrieve by date" or "retrieve by question" displayed in the bottom part of the screen, and thus, selects either "retrieve by date" or "retrieve by question". The former "retrieve by date" means that the retrieval item is specified by entering the date or dates or the term of answer data of the patient to be read on a screen (not shown) for specifying the date. The latter "retrieve by question" means that the retrieval item is specified by entering one or more question numbers of answer data of the patient to be read on a screen (not shown) for displaying the already-registered questions so as to select one or more of the displayed questions. After the end of entry of the patient, in step S45, the entered retrieval item is temporarily stored in the RAM 103. In step S46, the retrieval item temporarily stored in the RAM 103 is transmitted to the database server apparatus 30. In step S47, the answer data is received from the database server apparatus 30. In step S48, the line is disconnected from the database server apparatus 30. Then, in step S49, the answer data is displayed as shown in the center part of an example of screen of FIG. 27.

When the answer data is displayed, the date and time, the linking to a process for remedy policy entering, the goal, the question and the answer are displayed. As described above, the linking to the process for remedy policy entering is performed by a command operating section or command button 251 for giving a command to link to the entry of a remedy policy in the process for answer reading illustrated in FIG. 13 so as to jump directly to step S12 of the process for remedy policy entering and reading in conjunction with the patient code indicated by the patient number, and the medical doctor clicks on the command button 251 so as to select the linking. Then, in step S50, a judgment is made as to whether or not the linking is selected. If the linking is selected YES), the process flow proceeds to step S51, where the link code LC is set to 1, and thereafter, the process flow returns to the original main routine. If the linking is not selected in step S50 (NO), the process flow proceeds to step S52, where the medical doctor clicks on "end of processing" 254 so as to make a judgment as to whether or not the end of processing is selected. If the end of processing is selected (YES), the process flow proceeds to step S53, where the link code LC is reset to zero, and thereafter, the process flow returns to the original main routine. If the end of processing is not selected in step S52 (NO), the process flow returns to step S50.

FIG. 14 is a flowchart showing a process for remedy policy entering and reading (step S12) which is a subroutine of the process illustrated in FIG. 10.

In step S61 illustrated in FIG. 14, a line is first connected with the database server apparatus 30 through the communication network 50. In step S62, the patient information registered in the patient information memory 304a of the database server apparatus 30 is received. Then, in step S63, a screen of remedy policy entry and reading shown in FIG. 28, exclusive of remedy policy data in a lower part of the screen, is displayed. Then, in step S64, a judgment is made as to whether or not the link code LC is equal to 1, and the process flow jumps to step S67 if the link code LC is equal to 1 (YES), or the process flow proceeds to step S65 if the link code LC is not equal to 1 (NO). In step S65, patient selection is entered. For this entry, the patient selection is first performed by clicking the mouse 116b on a circle on the left side of the name of the selected one of a plurality of patients displayed in the patient selection. Then, in step S66, the selected patient code is temporarily stored in the RAM 103. In step S67, the selected patient code temporarily stored in the RAM 103 is transmitted to the database server apparatus 30. In step S68, the remedy policy data of the selected patient code is received from the database server apparatus 30. In step S69, the line is disconnected from the database server apparatus 30. Then, in step S70, past remedy policy data is displayed as shown in a center part of an example of screen of FIG. 28 so as to enter a mode capable of adding a new remedy policy with reference to the past remedy policy. In step S71, a medical doctor clicks on "addition" 252 for giving a command to enter an additional remedy policy, and thus, a judgment is made as to whether or not the addition is selected. If the addition is selected (YES), the process flow proceeds to step S73. If the addition is not selected (NO), the process flow proceeds to step S72. In step S72, the medical doctor clicks on the "end of process" 254 so as to make a judgment as to whether or not the end of processing is selected. If the end of processing is selected (YES), the process flow returns to the original main routine. If the end of processing is not selected (NO), the process flow returns to step S71.

In step S73, the medical doctor enters the remedy policy data using the keyboard 116a. If the medical doctor wants to clear the entered remedy policy, the medical doctor can click on "clear" 253 so as to clear the remedy policy. Then, in step S74, the remedy policy data is temporarily stored in the RAM 103. In step S75, the line is connected with the database server apparatus 30 through the communication network 50. Then, in step S76, the patient code and the remedy policy data temporarily stored in the RAM 103 are transmitted to the database server apparatus 30. Then, in step S77, the line is disconnected from the database server apparatus 30, and thereafter, the process flow returns to step S71.

The above-described process for remedy policy entering and reading has an advantage of making it possible to enter new remedy policy data remarkably easily without any errors, while viewing and referring to the past remedy policy data of the patient. In the processes illustrated in FIGS. 13 and 14, the click of the linking 251 allows the screen of answer reading shown in FIG. 27 to jump directly to the screen of remedy policy entry and reading of the patient shown in FIG. 24, which therefore makes it possible to display or enter the remedy policy and the like remarkably easily without performing the patient selection, so that the operationality can be greatly improved.

Figure 15:
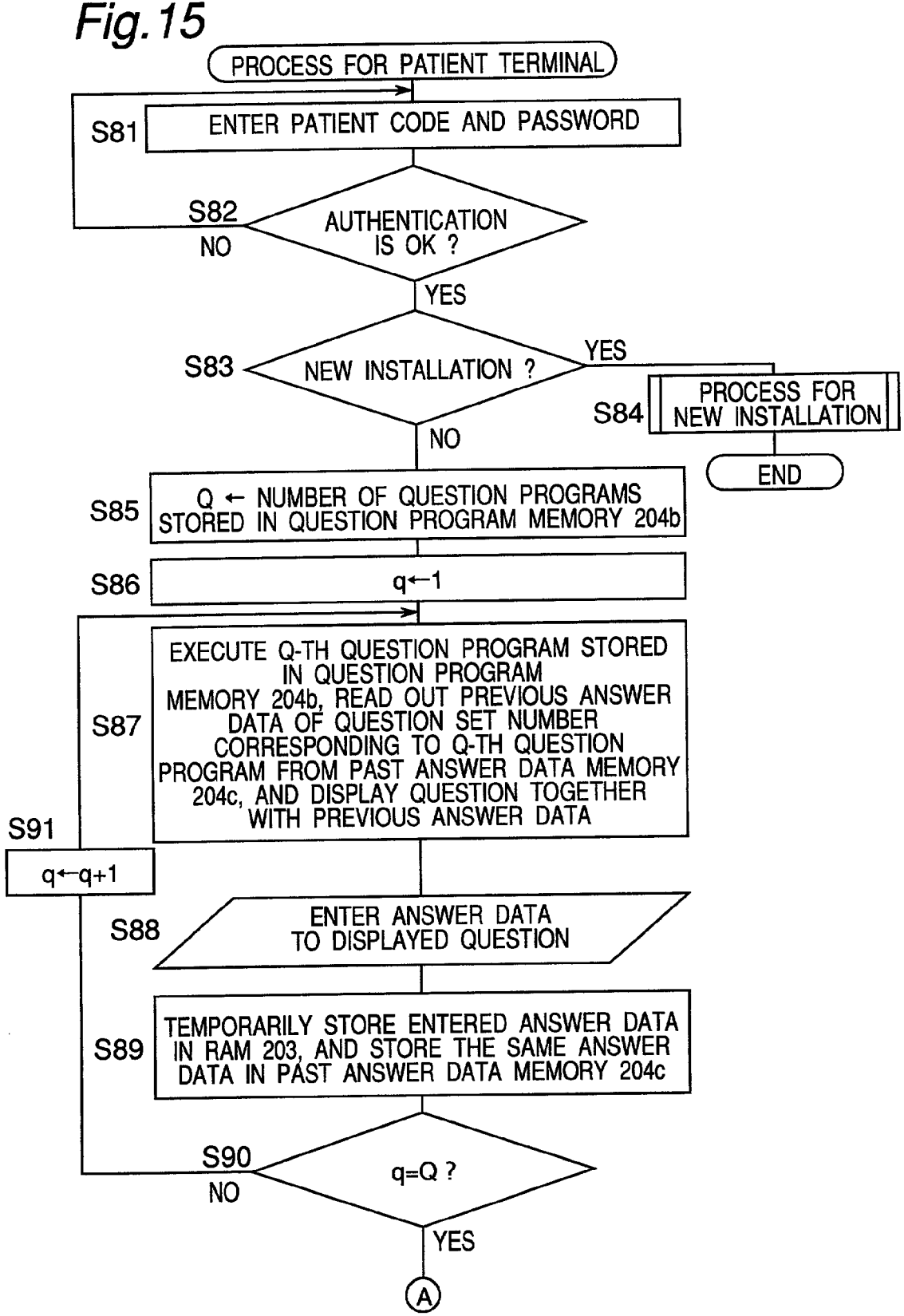
FIG. 15 is a flowchart illustrating a first part of a process for a patient terminal, which is performed by a main controller 201 of the patient terminal apparatus 20 shown in FIG. 3.
Figure 16:
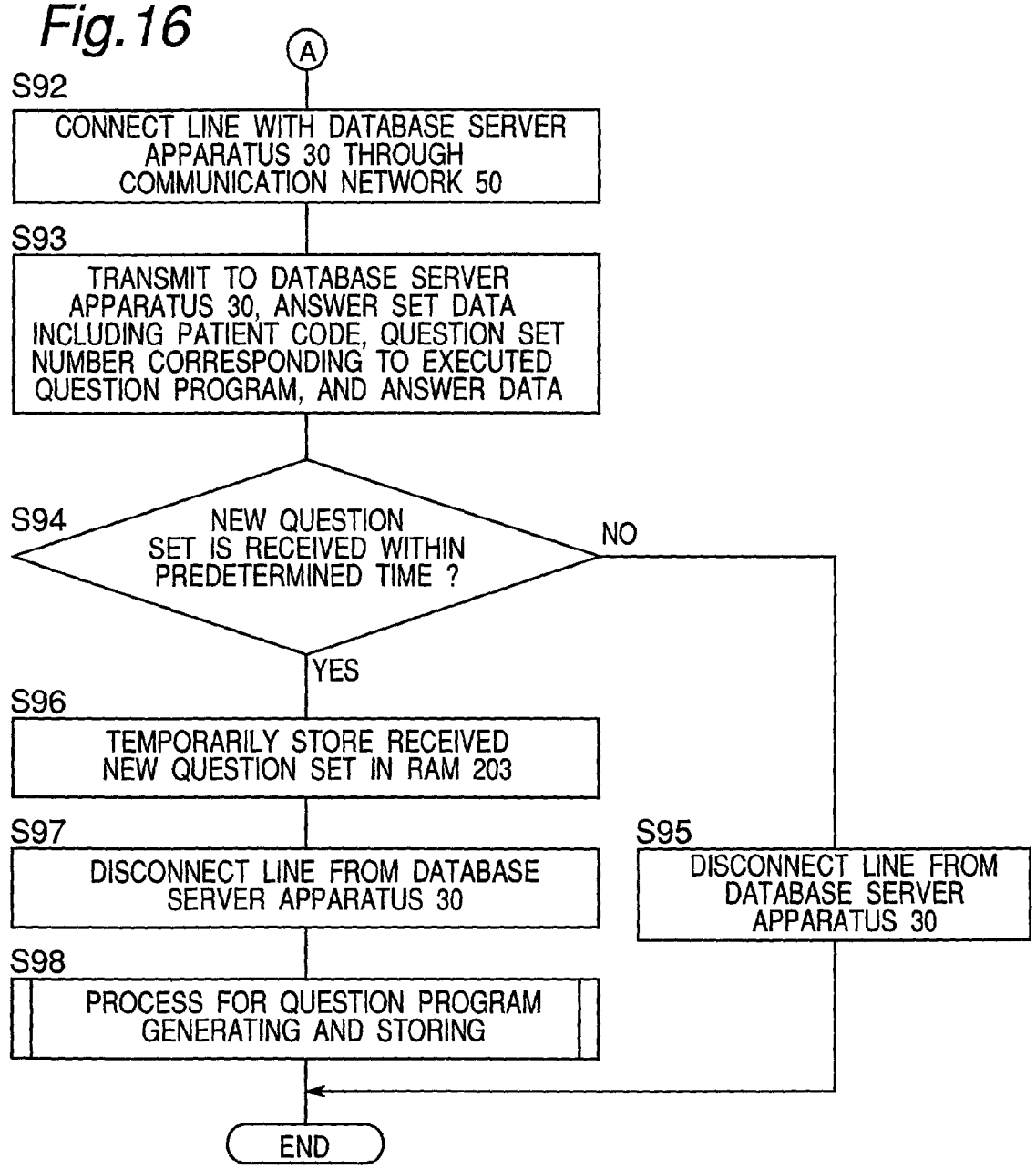
FIG. 16 is a flowchart illustrating a second part of the process for a patient terminal, which is executed by the main controller 201 of the patient terminal apparatus 20 shown in FIG. 3.

FIGS. 15 and 16 are flowcharts illustrating the process for the patient terminal which is executed by the main controller 201 of the patient terminal apparatus 20 shown in FIG. 3. In the process for the patient terminal, "entry" means that a patient enters data or a numerical value using the keyboard 216a or the mouse 216b shown in FIG. 3. "Display" means that image data from the main controller 201 shown in FIG. 3 is outputted to the liquid crystal display 215 through the display interface 205 and the output image data is displayed on the liquid crystal display 215.

Figure 17:
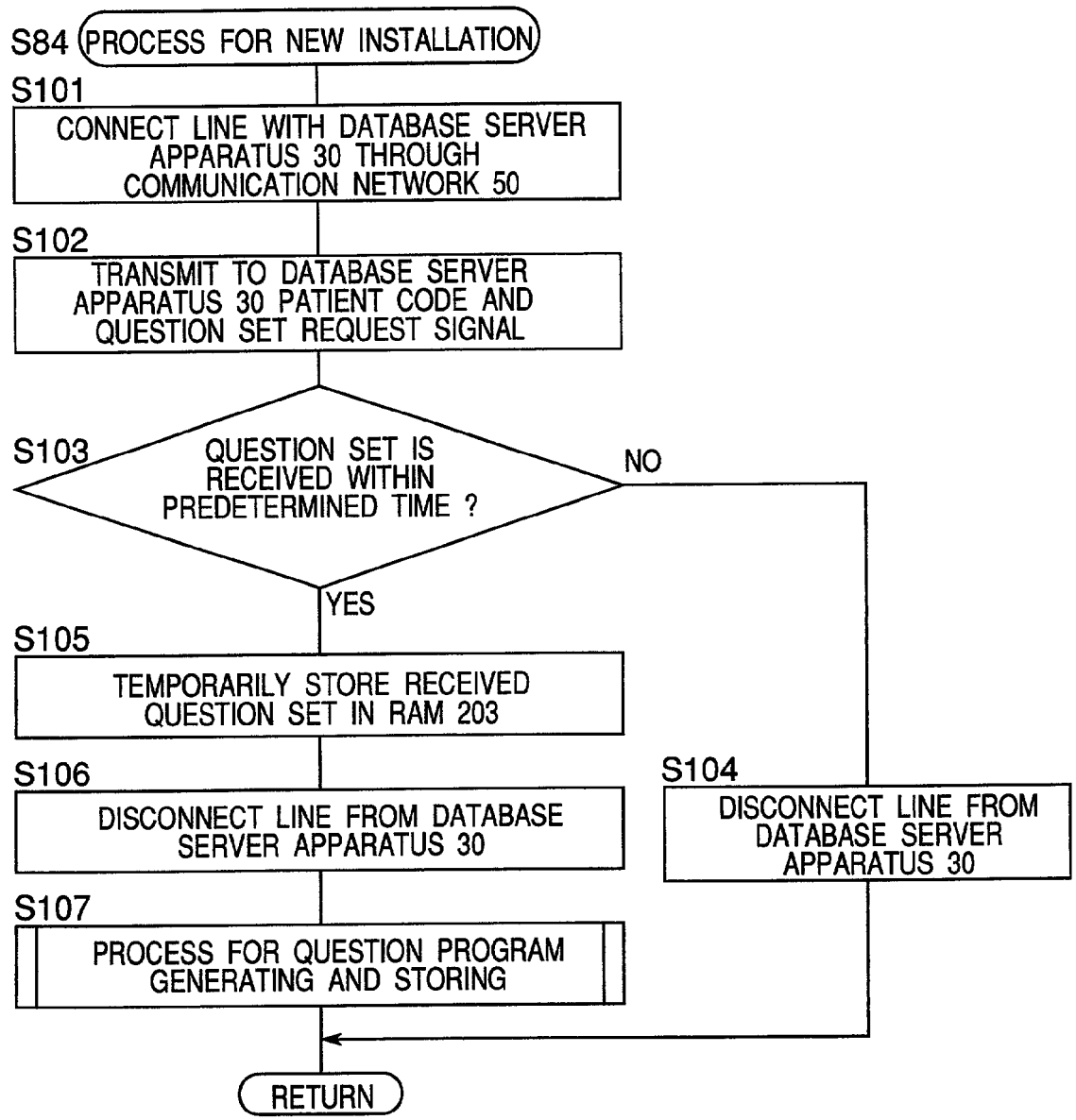
FIG. 17 is a flowchart illustrating a process for new installation (step S84) which is a subroutine of the process illustrated in FIG. 15.

In step S81 shown in FIG. 15, a patient code and a password are first entered. Then, in step S82, a judgment is made as to whether or not authentication is OK, that is, whether or not the entered patient code and password match authentication data previously entered and registered, and the process flow returns to step S81 if authentication is not OK (NO), or the process flow proceeds to step S83 if authentication is OK (YES). In step S83, a judgment is made as to whether or not the patient terminal apparatus 20 is a new installation. If the patient terminal apparatus 20 is the new installation (YES), the process goes to step S84, where a process for new installation illustrated in FIG. 17 is performed, and thereafter, the process for the patient terminal is ended. If the patient terminal apparatus 20 is not the new installation in step S83 (NO), the process flow proceeds to step S85.

In step S85, the number of question programs stored in the question program memory 204b is set to a constant parameter Q. In step S86, a variable parameter q is initialized to 1. Then, in step S87, the q-th question program stored in the question program memory 204b is executed, and previous answer data of the question set number corresponding to the q-th question program is read out from the past answer data memory 204c. Then, the corresponding predetermined question is displayed together with the previous answer data, as shown in any one of the examples of screens illustrated in FIGS. 29 to 38. In the preferred embodiment, the previous answer data is displayed, but the present invention is not limited to this preferred embodiment, and part or all of the previous answer data may be displayed.

In step S88, a patient enters answer data to the displayed question, and then clicks on "OK" 223, 225 or 234. Then, in step S89, the entered answer data is temporarily stored in the RAM 203, and the same answer data is stored in the past answer data memory 204c. In step S90, a judgment is made as to whether or not q is equal to Q. If q is not equal to Q (NO), the process goes to step S91, where the variable parameter q is incremented by one, and thereafter, the process flow returns to step S87. If q is equal to Q in step S90 (YES), the process flow proceeds to step S92 illustrated in FIG. 16.

In step S92 of FIG. 16, a line is connected with the database server apparatus 30 through the communication network 50. Then, in step S93, answer set data including the patient code, the question set number corresponding to the executed question program and the answer data is transmitted to the database server apparatus 30. In step S94, a judgment is made as to whether or not a new question set is received within a predetermined time (e.g., a few minutes), and the process flow proceeds to step S96 if the new question set is received (YES), or the process flow proceeds to step S95 if the new question set is not received (NO). In step S95, the line is disconnected from the database server apparatus 30, and thereafter, the process for the patient terminal is ended. In step S96, the received new question set is temporarily stored in the RAM 203. Then, in step S97, the line is disconnected from the database server apparatus 30. After that, in step S98, a process for question program generating and storing illustrated in FIG. 18 is performed, and thereafter, the process for patient terminal is ended.

FIG. 17 is a flowchart illustrating the process for new installation (step S84) which is a subroutine of the process illustrated in FIG. 15.

In step S101 illustrated in FIG. 17, a line is first connected with the database server apparatus 30 through the communication network 50. Then, in step S102, the patient code and a question set request signal are transmitted to the database server apparatus 30. In step S103, a judgment is made as to whether or not a question set is received within a predetermined time (e.g., a few minutes), and the process flow proceeds to step S105 if the question set is received (YES), or the process flow proceeds to step S104 if the question set is not received (NO). In step S104, the line is disconnected from the database server apparatus 30, and thereafter, the process flow returns to the original main routine. In step S105, the received question set is temporarily stored in the RAM 203. Then, in step S106, the line is disconnected from the database server apparatus 30. Then, in step S107, the process for question program generating and storing illustrated in FIG. 18 is performed, and thereafter, the process flow returns to the original main routine.

Figure 18:
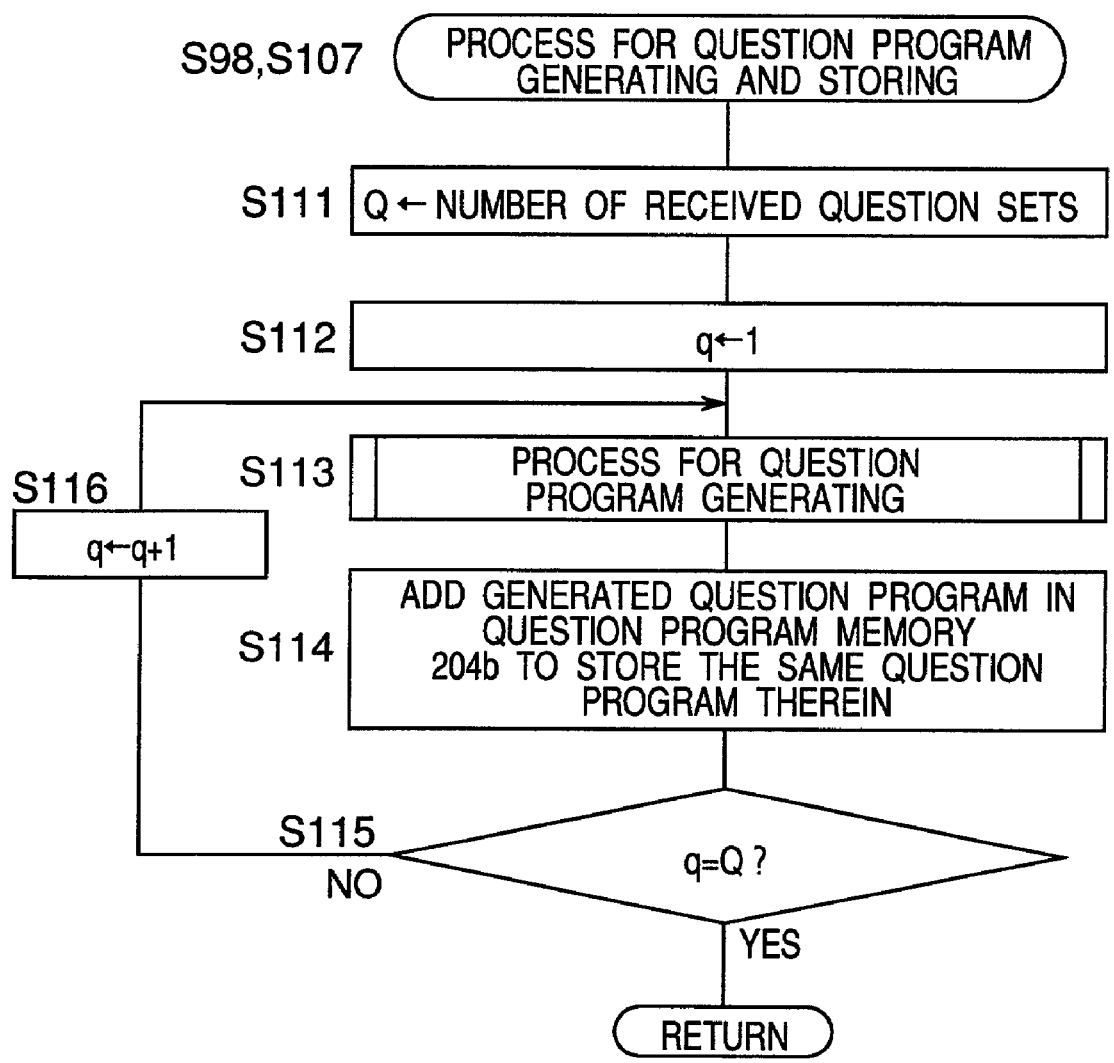
FIG. 18 is a flowchart illustrating a process for question program generating and storing (steps S98 and S107) which is a subroutine of the process illustrated in FIGS. 16 and 17.

FIG. 18 is a flowchart illustrating the process for question program generating and storing (steps S98 and S107) which is a subroutine of the process illustrated in FIGS. 16 and 17.

Figure 19:
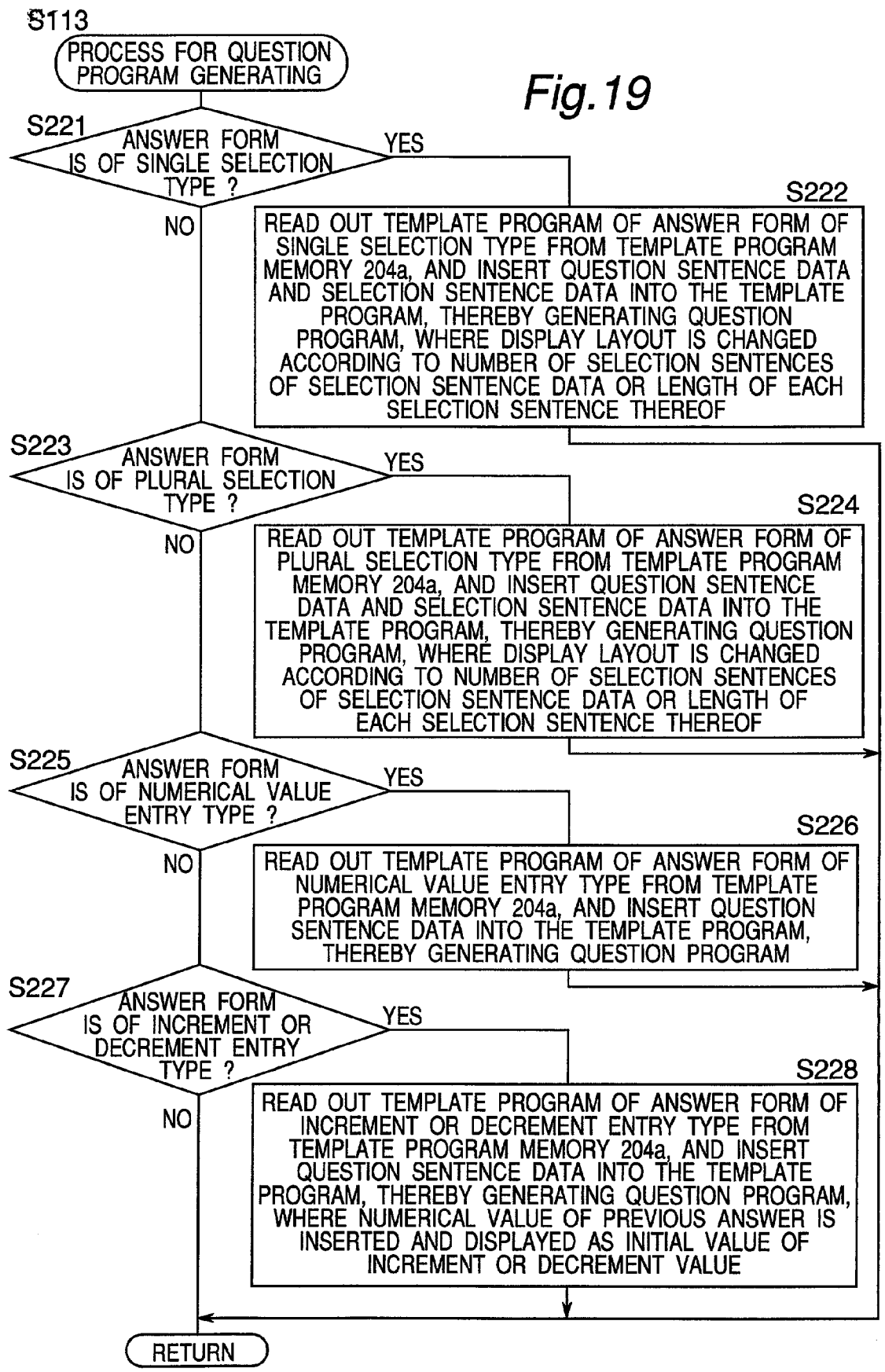
FIG. 19 is a flowchart illustrating a process for question program generating (step S113) which is a subroutine of the process illustrated in FIG. 18.

In step S111 illustrated in FIG. 18, the number of received question sets is set to the constant parameter Q. Then, in step S112, the variable parameter q is initialized to 1. Then, in step S113, a process for question program generating illustrated in FIG. 19 is performed. Then, in step S114, the generated question program is added to and stored in the question program memory 204b. In step S115, a judgment is made as to whether or not q is equal to Q. If q is not equal to Q in step S115 (NO), the process goes to step S116, where the variable parameter q is incremented by one, and thereafter, the process flow returns to step S113. If q is equal to Q in step S115 (YES), the process flow returns to the original main routine.

FIG. 19 is a flowchart illustrating the process for question program generating (step S113) which is a subroutine of the process illustrated in FIG. 18.

In step S221 illustrated in FIG. 19, a judgment is made as to whether or not the answer form is of the single selection type, and the process flow proceeds to step S222 if the answer form is of the single selection type (YES), or the process flow proceeds to step S223 if the answer form is not of the single selection type (NO). In step S222, a template program of the answer form of the single selection type is read out from the template program memory 204a, and question sentence data and selection sentence data are inserted into the template program, thereby generating a question program, and thereafter, the process flow returns to the original routine. More specifically, in the template program, the question sentence data and the selection sentence data are blank data, and thus, the question sentence data and the selection sentence data are inserted into the template program, thereby generating the question program for providing a screen which displays a question screen for the patient on the liquid crystal display 215 so as to allow the patient to enter an answer to the question. In other words, a display layout is changed according to the number of selection sentences of the selection sentence data or the length of each selection sentence thereof.

In a process for changing the display layout, when the number of selection sentences of the selection sentence data is equal to 2 and the length of each selection sentence thereof is short, the screen is configured to arrange two selection sentences in a row, as shown in the examples of the screen of FIG. 29 or 30. When the number of selection sentences of the selection sentence data is equal to 4 and the length of each selection sentence thereof is short, the screen is configured to arrange two selection sentences in each row, as shown in the examples of screens of FIGS. 31 and 32. However, when the number of selection sentences of the selection sentence data is plural, the length of each selection sentence thereof is relatively long and a row is substantially occupied by the selection sentence having the maximum length, the screen is configured to arrange one selection sentence in each row in a row direction. When the length of each selection sentence of the selection sentence data is longer and two or more rows are occupied by the selection sentence having the maximum length, the screen is configured to arrange each selection sentence in a plurality of rows and to arrange a plurality of selection sentences in the row direction. The above-described process for changing the display layout makes it possible to configure such a screen that the patient can easily grasp and view a plurality of answer examples when viewing the selection sentences of the answer examples.

Then, in step S223, a judgment is made as to whether or not the answer form is of the plural selection type, and the process flow proceeds to step S224 if the answer form is of the plural selection type (YES), or the process flow proceeds to step S225 if the answer form is not of the plural selection type (NO). In step S224, a template program of the answer form of the plural selection type is read out from the template program memory 204a, and question sentence data and selection sentence data are inserted into the template program, thereby generating a question program, and thereafter, the process flow returns to the original routine. In other words, the display layout is changed according to the number of selection sentences of the selection sentence data or the length of each selection sentence thereof in the same manner as the process of step S222. Examples of screens of this process are shown in FIGS. 33 and 34.

Then, in step S225, a judgment is made as to whether or not the answer form is of the numerical value entry type, and the process flow proceeds to step S226 if the answer form is of the numerical value entry type (YES), or the process flow proceeds to step S227 if the answer form is not of the numerical value entry type (NO). In step S226, a template program of the answer form of the numerical value entry type is read out from the template program memory 204a, and question sentence data is inserted into the template program, thereby generating a question program, and thereafter, the process flow returns to the original routine. Examples of screens of this process are shown in FIGS. 35 and 36.

In step S227, a judgment is made as to whether or not the answer form is of the increment or decrement entry type, and the process flow proceeds to step S228 if the answer form is of the increment or decrement entry type (YES), or the process flow returns to the original routine if the answer form is not of the increment or decrement entry type (NO). In step S228, a template program of the answer form of the increment or decrement entry type is read out from the template program memory 204a, and question sentence data is inserted into the template program, thereby generating a question program. Examples of screens of this process are shown in FIGS. 37 and 38, and a numerical value of a previous answer is inserted and displayed in the numerical value display 231 as an initial value of an increment or decrement entry value.

Next, a detailed description is given below with regard to the respective methods of displaying the examples of screens shown in FIGS. 29 to 34, except for the methods of displaying the examples of screens shown in FIGS. 24 to 28 and FIGS. 35 to 38 already described in detail.

FIG. 29 is a front view showing a question screen of the answer form SS1 of the single selection type (single selection from two answers with no goal), showing an example of a screen of the patient terminal apparatus 20 shown in FIG. 3. Referring to the example of screen shown in FIG. 29, the selection sentences of the answer examples to the question sentence "do you have headache?" are "yes" and "no", and the previous answer "no" is displayed in the bottom left part of the screen.

FIG. 30 is a front view showing a question screen of the answer form SS2 of the single selection type (single selection from two answers with a goal), showing an example of a screen of the patient terminal apparatus 20 shown in FIG. 3. Referring to the example of the screen shown in FIG. 30, the selection sentences of the answer examples to the question sentence "did you do exercise for 30 minutes or more?" are "yes" and "no", the previous answer "no" is displayed in the bottom left part of the screen, and the goal "yes" is displayed in the bottom right part of the screen.

FIG. 31 is a front view showing a question screen of the answer form SS3 of the single selection type (single selection from four answers with no goal), showing an example of a screen of the patient terminal apparatus 20 shown in FIG. 3. Referring to the example of the screen shown in FIG. 31, the selection sentences of the answer examples to the question sentence "did you sleep well last night?" are the following four sentences:
 (a) slept well;
 (b) slept;
 (c) slept little; and
 (d) Not slept.

The previous answer "slept" is displayed in the bottom left part of the screen.

FIG. 32 is a front view showing a question screen of the answer form SS4 of the single selection type (single selection from four answers with a goal), showing an example of a screen of the patient terminal apparatus 20 shown in FIG. 3. Referring to the example of the screen shown in FIG. 32, the selection sentences of the answer examples to the question sentence "did you drink beer?" are the following four sentences:
 (a) less than 1;
 (b) less than 2;
 (c) less than 3; and
 (d) 3 or more.

The previous answer "less than 1" is displayed in the bottom left part of the screen, and the goal "less than 1" is displayed in the bottom right part of the screen.

FIG. 33 is a front view showing a question screen of the answer form PS1 of the plural selection type (with no goal), showing an example of a screen of the patent terminal apparatus 20 shown in FIG. 3. Referring to the example of the screen shown in FIG. 33, the selection sentences of the answer examples to the question sentence "which time period did you feel badly?" are the following four sentences:
 (a) 0:00-6:00;
 (b) 6:00-12:00;
 (c) 12:00-18:00; and
 (d) 18:00-24:00.

The previous answer "6:00-12:00, 18:00-24:00" is displayed in the bottom left part of the screen.

FIG. 34 is a front view showing a question screen of the answer form PS2 of the plural selection type (with a goal), showing an example of a screen of the patient terminal apparatus 20 shown in FIG. 3. Referring to the example of the screen shown in FIG. 34, the selection sentences of the answer examples to the question sentence "which food did you eat today?" are the following six sentences:
 (a) grain;
 (b) meat;
 (c) fish;
 (d) dairy products;
 (e) vegetables; and
 (f) fruits.

The previous answer "grain, meat, vegetables, fruits" is displayed in the bottom left part of the screen, and the goal "all" is displayed in the bottom right part of the screen.

Figure 20:
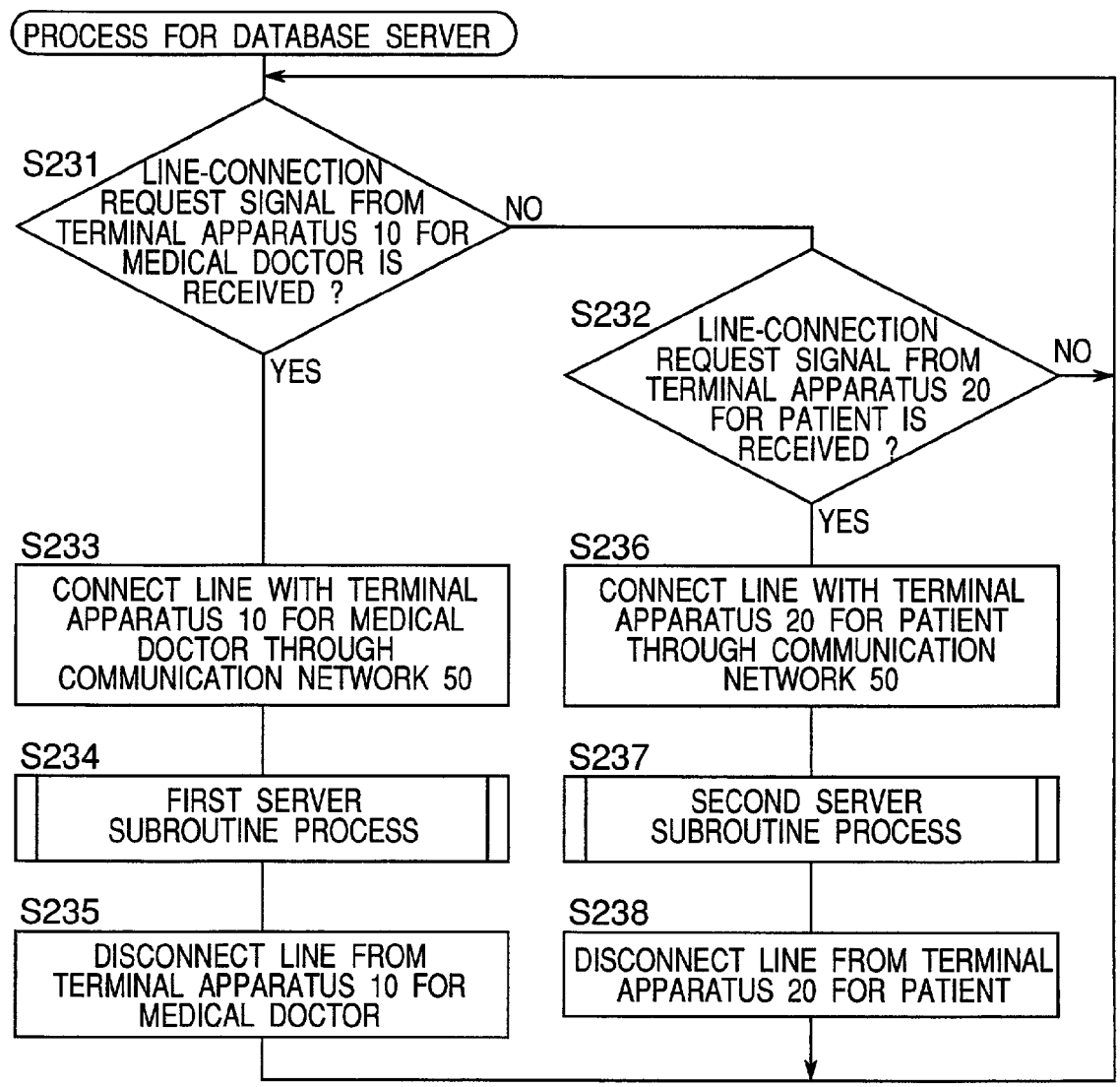
FIG. 20 is a flowchart illustrating a process for a database server, which is performed by a main controller 301 of the database server apparatus 30 shown in FIG. 4.

FIG. 20 is a flowchart illustrating the process for the database server, which is executed by the main controller 301 of the database server apparatus 30 shown in FIG. 4.

Figure 21:
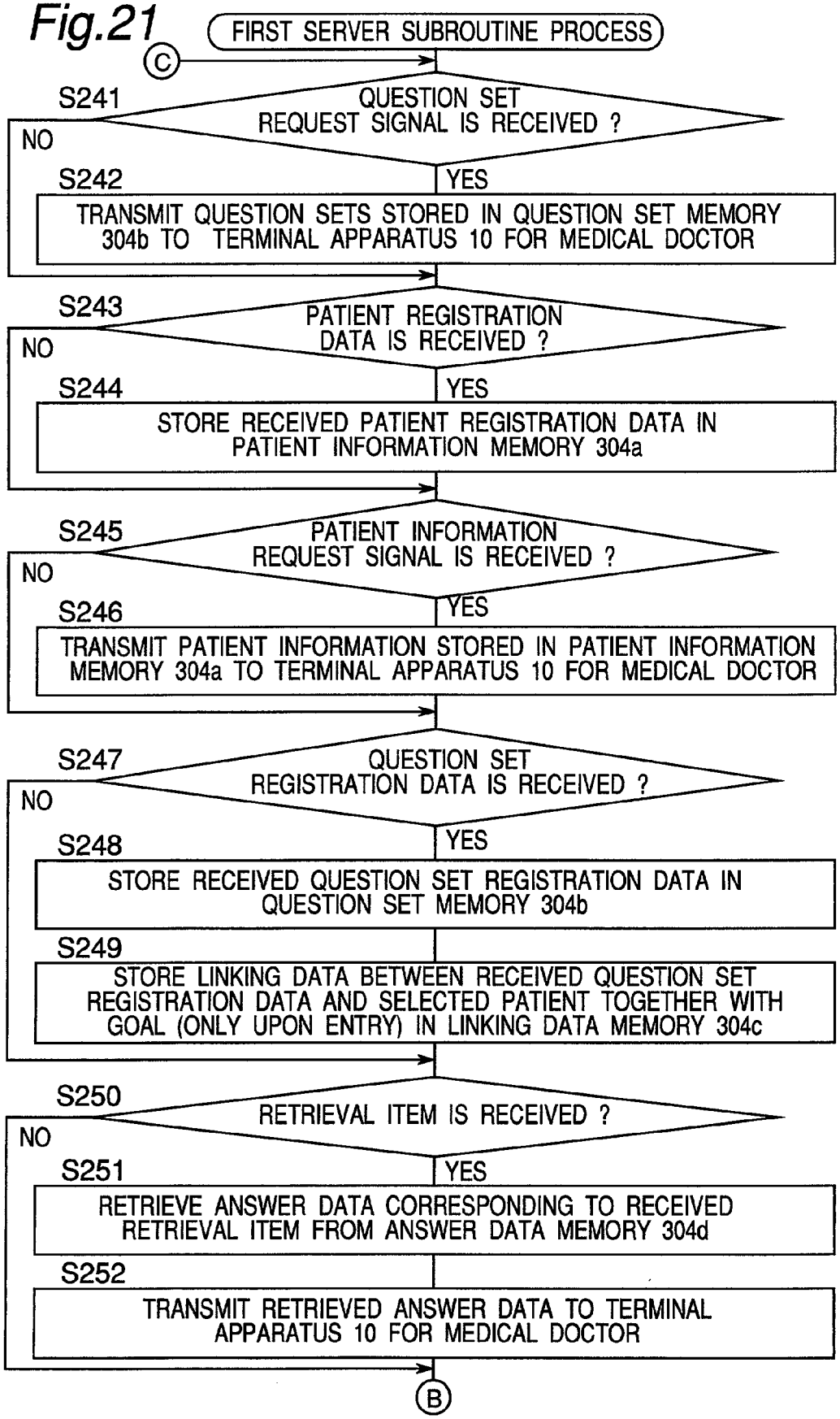
FIG. 21 is a flowchart illustrating a first part of a first server subroutine process (step S234) which is a subroutine of the process illustrated in FIG. 20.
Figure 22:
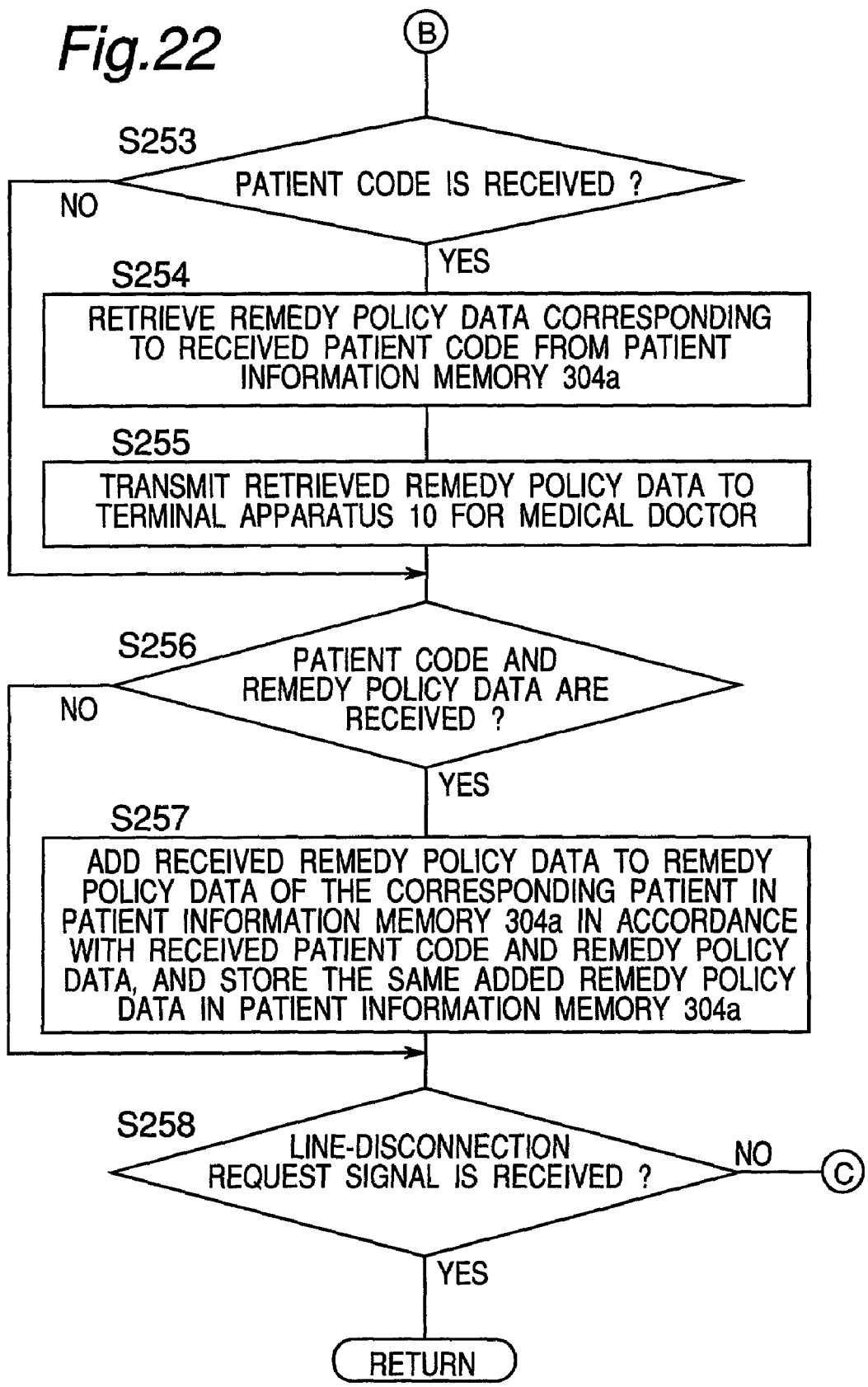
FIG. 22 is a flowchart illustrating a second part of the first server subroutine process (step S234) which is a subroutine of the process illustrated in FIG. 20.
Figure 23:
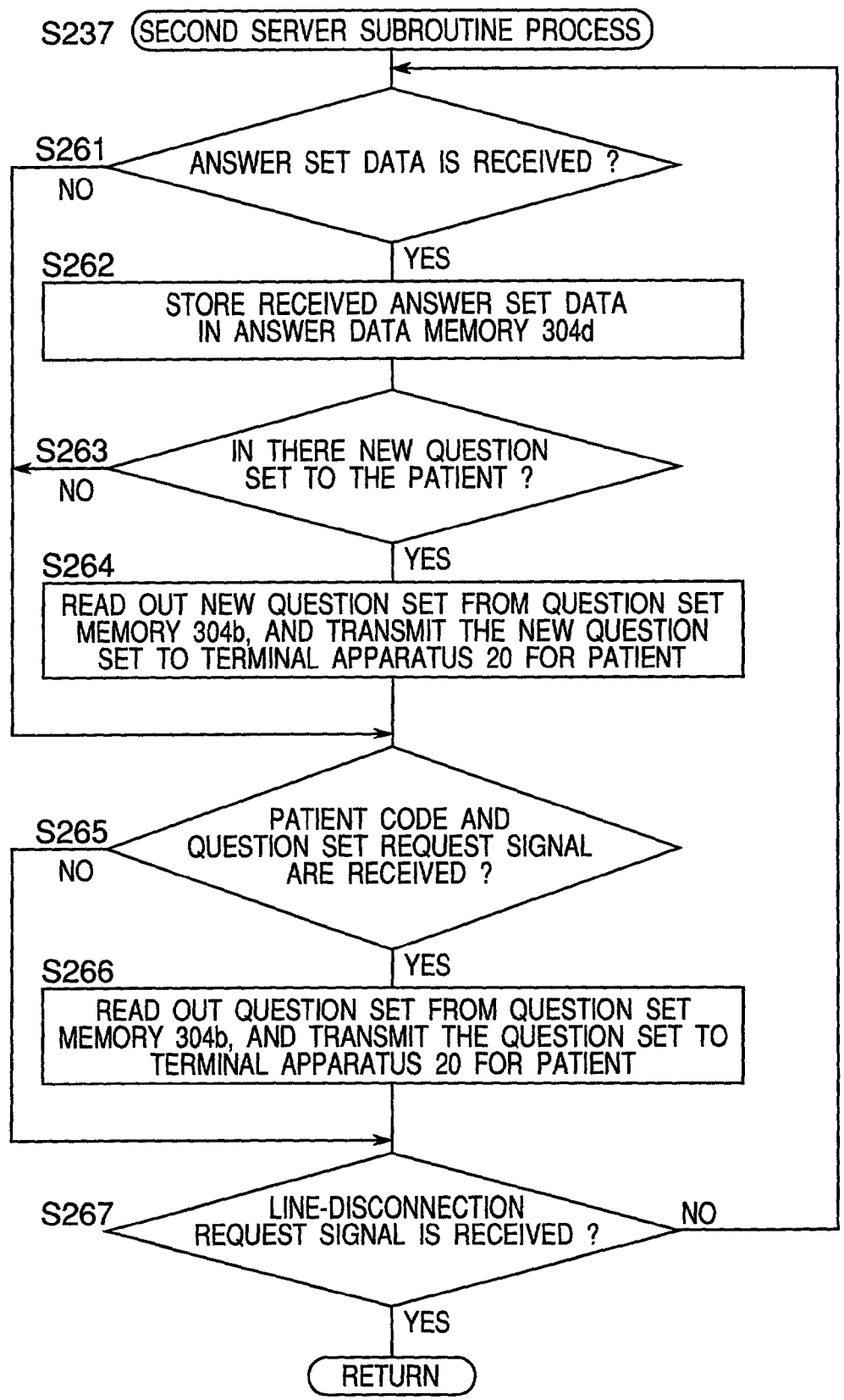
FIG. 23 is a flowchart illustrating a second server subroutine process (step S237) which is a subroutine of the process illustrated in FIG. 20.

In step S231 illustrated in FIG. 20, a judgment is made as to whether or not a line-connection request signal from the medical doctor terminal apparatus 10 is received, and the process flow proceeds to step S233 if the line-connection request signal is received (YES), or the process flow proceeds to step S232 if the line-connection request signal is not received (NO). Then, in step S232, a judgment is made as to whether or not a line-connection request signal from the patient terminal apparatus 20 is received, and the process flow proceeds to step S236 if the line-connection request signal is received (YES), or the process flow returns to step S231 if the line-connection request signal is not received (NO). In step S233, a line is connected with the medical doctor terminal apparatus 10 through the communication network 50. In step S234, a first server subroutine process illustrated in FIGS. 21 and 22 is performed. After that, in step S235, the line is disconnected from the medical doctor terminal apparatus 10, and the process flow returns to step S231. In step S236, a line is connected with the patient terminal apparatus 20 through the communication network 50. In step S237, a second server subroutine process illustrated in FIG. 23 is performed. After that, in step S238, the line is disconnected from the patient terminal apparatus 20, and the process flow returns to step S231.

FIGS. 21 and 22 are flowcharts illustrating the first server subroutine process (step S234) which is a subroutine of the process illustrated in FIG. 20.

In step S241 illustrated in FIG. 21, a judgment is made as to whether or not a question set request signal is received, and the process flow proceeds to step S242 if the question set request signal is received (YES), or the process flow proceeds to step S243 if the question set request signal is not received (NO). In step S242, the question sets stored in the question set memory 304b are transmitted to the medical doctor terminal apparatus 10, and thereafter, the process flow proceeds to step S243. Then, in step S243, a judgment is made as to whether or not patient registration data is received, and the process flow proceeds to step S244 if the patient registration data is received (YES), or the process flow proceeds to step S245 if the patient registration data is not received (NO). In step S244, the received patient registration data is stored in the patient information memory 304a, and thereafter, the process flow proceeds to step S245. Then, in step S245, a judgment is made as to whether or not a patient information request signal is received, and the process flow proceeds to step S246 if the patient information request signal is received (YES), or the process flow proceeds to step S247 if the patient information request signal is not received (NO). In step S246, patient information stored in the patient information memory 304a is transmitted to the medical doctor terminal apparatus 10, and thereafter, the process flow proceeds to step S247. Then, in step S247, a judgment is made as to whether or not question set registration data is received, and the process flow proceeds to step S248 if the question set registration data is received (YES), or the process flow proceeds to step S250 if the question set registration data is not received (NO). In step S248, the received question set registration data is stored in the question set memory 304b. In step S249, linking data between the received question set registration data and the selected patient, in conjunction with the goal (only when the goal is entered), is stored in the linking data memory 304c, and thereafter, the process flow proceeds to step S250. Then, in step S250, a judgment is made as to whether or not a retrieval item is received, and the process flow proceeds to step S251 if the retrieval item is received (YES), or the process flow proceeds to step S253 of FIG. 22 if the retrieval item is not received (NO). In step S251, answer data corresponding to the received retrieval item is retrieved from the answer data memory 304d. In step S252, the retrieved answer data is transmitted to the medical doctor terminal apparatus 10, and thereafter, the process flow proceeds to step S253 of FIG. 22.

In step S253 of FIG. 22, a judgment is made as to whether or not a patient code is received, and the process flow proceeds to step S254 if the patient code is received (YES), or the process flow proceeds to step S256 if the patient code is not received (NO). In step S254, remedy policy data corresponding to the received patient code (i.e., the patient number) is retrieved from the patient information memory 304a. In step S255, the retrieved remedy policy data is transmitted to the medical doctor terminal apparatus 10, and thereafter, the process flow proceeds to step S256. Then, in step S256, a judgment is made as to whether or not the patient code and the remedy policy data are received, and the process flow proceeds to step S257 if the patient code and the remedy policy data are received (YES), or the process flow proceeds to step S258 if the patient code and the remedy policy data are not received (NO). In step S257, the received remedy policy data is added to the remedy policy data of the corresponding patient in the patient information memory 304a in accordance with the received patient code and remedy policy data, and the same added remedy policy data is stored in the patient information memory 304a. After that, the process flow proceeds to step S258. In step S258, a judgment is made as to whether or not a line-disconnection request signal is received, and the process flow returns to the original main routine if the line-disconnection request signal is received (YES), or the process flow returns to step S241 if the line-disconnection request signal is not received (NO).

FIG. 23 is a flowchart illustrating the second server subroutine process (step S237) which is a subroutine of the process illustrated in FIG. 20.

In step S261 illustrated in FIG. 23, a judgment is first made as to whether or not answer set data is received, and the process flow proceeds to step S262 if the answer set data is received (YES), or the process flow proceeds to step S265 if the answer set data is not received (NO). In step S262, the received answer set data is stored in the answer data memory 304d. In step S263, a judgment is made as to whether or not a new question set which is not yet transmitted to the patient terminal apparatus 20 of the corresponding patient is present in the hard disk memory 304, and the process flow proceeds to step S264 if the new question set is present (YES), or the process flow proceeds to step S265 if the new question set is not present (NO). In step S264, the new question set is read out from the question set memory 304b, and the new question set is transmitted to the patient terminal apparatus 20. After that, the process flow proceeds to step S265. Then, in step S265, a judgment is made as to whether or not the patient code and the question set request signal are received, and the process flow proceeds to step S266 if the patient code and the question set request signal are received (YES), or the process flow proceeds to step S267 if the patient code and the question set request signal are not received (NO). In step S266, the question set is read out from the question set memory 304b, and the question set is transmitted to the terminal apparatus 20 for patient. After that, the process flow proceeds to step S267. In step S267, a judgment is made as to whether or not a line-disconnection request signal is received, and the process flow returns to the original main routine if the line-disconnection request signal is received (YES), or the process flow returns to step S261 if the line-disconnection request signal is not received (NO).

APPLICABILITY OF INDUSTRIAL UTILIZATION

As described in detail above, the communication system 1 for providing information of a medical doctor's questions to patients according to the present invention includes the plurality of medical doctor terminal apparatus 10, the patient terminal apparatus 20, and the database server apparatus 30 for storing question sets for medical doctor's questions to patients, where the medical doctor terminal apparatus 10, the patient terminal apparatus 20 and the database server apparatus 30 are connected to each other through the communication network 50. More specifically, the patient terminal apparatus 20 generates question programs for making inquiries about a medical doctor's questions to patients in accordance with the question sets received from the database server apparatus 30, displays the questions for the medical doctor's questions to patients by execution of the generated question programs, enters answer data to the displayed questions, transmits the entered answer data to the database server apparatus, and stores the transmitted answer data in the database server apparatus. The medical doctor terminal apparatus 10 receives the stored answer data by accessing the database server apparatus, and displays the received answer data.

On the other hand, the systems of the prior art are configured to transmit the question programs in themselves through the communication network so as to provide the question programs for a medical doctor's questions to patients.

However, according to the present invention, the patient terminal apparatus 20 generates the question programs in accordance with the question sets received from the database server apparatus 30, and executes the generated question programs. Therefore, the question programs in themselves are not transmitted through the communication network, so that the system of the present invention can retain the security of questions to patients, as compared to the systems of the prior art.

Moreover, the patient terminal apparatus 20 stores the template question programs corresponding to the predetermined answer forms, and can generate the question programs remarkably easily by inserting question sets received from the database server apparatus 30 into the template question programs.

What is claimed is:

1. A communication system for providing information of a medical doctor's questions to patients, said communication system comprising a medical doctor terminal apparatus, a patient terminal apparatus, and a database server apparatus for storing question set data for the medical doctor's questions to patients, said medical doctor terminal apparatus, said patient terminal apparatus and said database server apparatus are connected to each other through a communication network, wherein said patient terminal apparatus comprises:
- first interface means for establishing a network connection and data communication between the database server apparatus and said patient terminal apparatus via the communication network;
- first receiving means for receiving question set data from said database server apparatus, the question set data being dependent on a particular patient among a plurality of patients;
- template storing means for storing template programs which correspond to predetermined forms used to present questions to be answered by a patient, the template programs are not dependent on a particular patient;
- generating means for generating, upon receiving the question set data from said database server apparatus, question programs that create the forms which are dependent on a particular patient among a plurality of patients using a patient-independent template program from among the template programs stored in the template storing means so that patient-dependent question programs and forms are not transmitted through the communication network, the forms being created on the patient terminal by inserting the question set data received from said database server apparatus into the template programs, thereby retaining security of the questions to patients, the question programs being generated for providing medical doctor's questions to patients;
- displaying means for displaying questions for the medical doctor's questions to patients by executing the question programs generated by said generating means;
- entering means for entering answer data to the displayed questions; and
- transmitting means for transmitting the entered answer data to said database server apparatus, and storing the transmitted answer data in said database server apparatus; and
- second interface means for terminating the network connection and data communication between the database server apparatus and said patient terminal apparatus;
- wherein said medical doctor terminal apparatus comprises second receiving means for receiving the answer data stored in said database server apparatus by accessing said database server apparatus, and displaying the received answer data, and
- wherein the patient dependent question programs are not transmitted through the communication network.

2. The system as claimed in claim 1, wherein each of the question set data includes data indicative of an answer form, and a question sentence.

3. The system as claimed in claim 2, wherein each of the question set data further includes data indicative of at least one selection sentence.

4. The system as claimed in claim 2, wherein each of the question set data further includes data indicative of a goal answer entered by a medical doctor.

5. The system as claimed in claim 1, wherein:
- said patient terminal apparatus further comprises answer data storing means for storing entered past answer data; and
- said displaying means displays past answer data stored in said answer data storing means in conjunction with a question.

6. The system as claimed in claim 3, wherein said generating means comprises changing means for changing a display layout of the at least one selection sentence according to at least one of a number of selection sentences and a length of each selection sentence.

7. The system as claimed in claim 1, wherein said medical doctor terminal apparatus further comprises:
- transmitting and storing means for entering a remedy policy for a patient, transmitting the entered remedy policy to said database server apparatus, and storing the transmitted remedy policy in said database server apparatus; and
- third receiving means for receiving the stored remedy policy for the patient by accessing said database server apparatus, and displaying the received remedy policy.

8. The system as claimed in claim 7, wherein said medical doctor terminal apparatus further comprises link controlling means for controlling said third receiving means in accordance with a command from an operator so that said third receiving means receives the stored remedy policy for the patient by accessing said database server apparatus and displays the received remedy policy, when said second receiving means receives the answer data and displays the received answer data.

9. The system as claimed in claim 1, wherein said database server apparatus comprises:
- first storing means for storing information about each respective patient;
- second storing means for storing questions for medical doctor's questions for each respective question;
- third storing means for storing information about linking between the respective patients and respective questions; and
- fourth storing means for storing answer data from said patient terminal apparatus.

10. The system as claimed in claim 9, wherein said third storing means further stores a goal answer entered by a medical doctor, in addition to the information about linking between the respective patients and respective questions.

11. A patient terminal apparatus for use in a communication system for providing information of a medical doctor's questions to patients, the communication system comprising a medical doctor terminal apparatus, said patient terminal apparatus, and a database server apparatus for storing question set data for the medical doctor's questions to patients, said patient terminal apparatus, the medical doctor terminal apparatus and the database server apparatus being connected to each other through a communication network, said patient terminal apparatus comprising:
- first interface means for establishing a network connection and data communication between the database server apparatus and said patient terminal apparatus via the communication network;
- receiving means for receiving question set data from the database server apparatus, the question set data being dependent on a particular patient among a plurality of patients;
- template storing means for storing template programs which correspond to predetermined forms used to present questions to be answered by a patient, the template programs are not dependent on a particular patient;
- generating means for generating, upon receiving the question set data from said database server apparatus, question programs that create the forms which are dependent on a particular patient among a plurality of patients using a patient-independent template program from among the template programs stored in the template storing means so that patient-dependent question programs and forms are not transmitted through the communication network, the forms being created on the patient terminal by inserting the question set data received from said database server apparatus into the template programs, thereby retaining security of the questions to patients, the question programs being generated for providing medical doctor's questions to patients;

displaying means for displaying questions for the medical doctor's questions to patients by executing the question programs generated by said generating means;

entering means for entering answer data to the displayed questions; and transmitting means for transmitting the entered answer data to the database server apparatus and storing the transmitted answer data in the database server apparatus; and second interface means for terminating the network connection and data communication between the database server apparatus and said patient terminal apparatus, wherein the patient dependent question programs are not transmitted through the communication network.

12. The patient terminal apparatus as claimed in claim 11, wherein each of the question set data includes data indicative of an answer form, and a question sentence.

13. The patient terminal apparatus as claimed in claim 12, wherein each of the question set data further includes data indicative of at least one selection sentence.

14. The patient terminal apparatus as claimed in claim 12, wherein each of the question set data further includes data indicative of a goal answer entered by a medical doctor.

15. The patient terminal apparatus as claimed in claim 11, further comprising answer data storing means for storing entered past answer data, wherein said displaying means displays past answer data stored in said answer data storing means in conjunction with a question.

16. The patient terminal apparatus as claimed in claim 13, wherein said generating means comprises changing means for changing a display layout of the at least one selection sentence according to at least one of a number of selection sentences and a length of each selection sentence.

17. The system as claimed in claim 1, wherein template storing means stores template question programs which correspond to predetermined answer forms and are not dependent on a particular patient, and wherein the generating means generates question programs which are dependent on a particular patient among a plurality of patients, by inserting question set data received from said database server apparatus into the template question programs.

18. The patient terminal apparatus as claimed in claim 11, wherein the template storing means stores template question programs which correspond to predetermined answer forms and are not dependent on a particular patient, and wherein the generating means for generates question programs which are dependent on a particular patient among a plurality of patients, by inserting question set data received from said database server apparatus into the template question programs.

19. The system as claimed in claim 17, wherein the forms include at least one of:
(a) a first answer form for answering by selecting at least one among a plurality of selection sentences of answers as an answer to a question; and
(b) a second answer form for answering by using a numerical value as an answer to the question.

20. The patient terminal apparatus as claimed in claim 18, wherein the forms include at least one of:
(a) a first answer form for answering by selecting at least one among a plurality of selection sentences of answers as an answer to a question; and
(b) a second answer form for answering by using a numerical value as an answer to the question.

21. The system as claimed in claim 19, wherein the second answer form includes at least one of:
(a) a third answer form for answering by directly entering a numerical value as an answer to the question; and
(b) a fourth answer form for answering by entering a numerical value indicative of an answer with either one of increasing and decreasing a numerical value starting at an initial value, as an answer to the question.

22. The system as claimed in claim 21, wherein:
said patient terminal apparatus further comprises answer data storing means for storing entered past answer data; and
the initial value of the numerical value is a numerical value indicative of a previous answer of the particular patient included in the past answer data stored in said answer data storing means.

23. The patient terminal apparatus as claimed in claim 20, wherein the second answer form includes at least one of:
(a) a third answer form for answering by directly entering a numerical value as an answer to the question; and
(b) a fourth answer form for answering by entering a numerical value indicative of an answer with either one of increasing and decreasing a numerical value starting at an initial value as an answer to the question.

24. The patient terminal apparatus as claimed in claim 23, further comprising answer data storing means for storing entered past answer data, wherein the initial value of the numerical value is a numerical value indicative of a previous answer of the particular patient included in the past answer data stored in said answer data storing means.

* * * * *

UNITED STATES PATENT AND TRADEMARK OFFICE
CERTIFICATE OF CORRECTION

PATENT NO. : 7,603,282 B2  Page 1 of 1
APPLICATION NO. : 10/058732
DATED : October 13, 2009
INVENTOR(S) : Imai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1229 days.

Signed and Sealed this

Fifth Day of October, 2010

David J. Kappos
*Director of the United States Patent and Trademark Office*